United States Patent
Guillemont et al.

(10) Patent No.: US 8,623,872 B2
(45) Date of Patent: Jan. 7, 2014

(54) QUINAZOLINONE DERIVATIVES AS PARP INHIBITORS

(75) Inventors: Jérôme Emile Georges Guillemont, Ande (FR); Ludo Edmond Josephine Kennis, Lier (BE); Josephus Carolus Mertens, Oud-Turnhout (BE); Jacobus Alphonsus Josephus Van Dun, Kasterlee (BE); Maria Victorina Francisca Somers, Vosselaar (BE); Walter Boudewijn Leopold Wouters, Kapellen (BE)

(73) Assignee: Janssen Pharmaceutica, NV (BE)

( * ) Notice: Subject to any disclaimer, the term of this patent is extended or adjusted under 35 U.S.C. 154(b) by 1251 days.

(21) Appl. No.: 11/569,892

(22) PCT Filed: Jun. 28, 2005

(86) PCT No.: PCT/EP2005/053029
§ 371 (c)(1),
(2), (4) Date: Dec. 1, 2006

(87) PCT Pub. No.: WO2006/003146
PCT Pub. Date: Jan. 12, 2006

(65) Prior Publication Data
US 2008/0070915 A1    Mar. 20, 2008

(30) Foreign Application Priority Data
Jun. 30, 2004  (EP) .................................. 04076887

(51) Int. Cl.
*A61K 31/497*   (2006.01)
*C07D 239/72*   (2006.01)

(52) U.S. Cl.
USPC ................. 514/252.16; 514/254.06; 544/283

(58) Field of Classification Search
None
See application file for complete search history.

(56) References Cited

U.S. PATENT DOCUMENTS

| | | | |
|---|---|---|---|
| 3,274,194 A | 9/1966 | Hayao et al. |
| 3,753,988 A | 8/1973 | Rodway et al. |
| 3,879,393 A | 4/1975 | Havera |
| 3,919,425 A | 11/1975 | Vidrio |
| 4,335,127 A | 6/1982 | Vandenberk et al. |
| 5,028,606 A | 7/1991 | Venet et al. |
| 5,118,684 A | 6/1992 | Sugimoto et al. |
| 5,151,421 A | 9/1992 | Venet et al. |
| 5,177,075 A | 1/1993 | Suto et al. |
| 5,231,184 A | 7/1993 | Stokbroekx et al. |
| 5,304,560 A | 4/1994 | Shimazaki et al. |
| 5,374,637 A | 12/1994 | Van Daele et al. |
| 6,344,449 B1 | 2/2002 | Rudolf et al. |
| 6,583,144 B2 | 6/2003 | Ohkura et al. |
| 6,635,642 B1 | 10/2003 | Jackson et al. |
| 7,115,630 B2 | 10/2006 | Mabire et al. |
| 7,498,325 B2 | 3/2009 | Rudolf et al. |
| 7,928,104 B2 | 4/2011 | Mabire et al. |
| 8,198,448 B2 | 6/2012 | Albrecht et al. |
| 2001/0036946 A1 | 11/2001 | Rudolf et al. |
| 2002/0002174 A1 | 1/2002 | Nieduzak et al. |
| 2003/0069231 A1 | 4/2003 | Rudolf et al. |
| 2003/0130505 A1 | 7/2003 | Zhi et al. |
| 2003/0225268 A1 | 12/2003 | Bunnelle et al. |
| 2004/0077667 A1 | 4/2004 | Matsuoka et al. |
| 2004/0176361 A1 | 9/2004 | Fujio et al. |
| 2005/0256000 A1 | 11/2005 | Schaper et al. |
| 2008/0039480 A1 | 2/2008 | Kennis et al. |
| 2008/0269234 A1 | 10/2008 | Gandhi et al. |
| 2009/0048259 A1 | 2/2009 | Austin et al. |
| 2009/0163480 A1 | 6/2009 | Rudolf et al. |
| 2009/0292121 A1 | 11/2009 | Morioka et al. |
| 2012/0046274 A1 | 2/2012 | Mabire et al. |

FOREIGN PATENT DOCUMENTS

| | | |
|---|---|---|
| DE | 1006423 | 4/1957 |
| EP | 0013612 A | 11/1983 |
| EP | 0156433 | 10/1985 |
| EP | 0229391 A1 | 7/1987 |
| EP | 0391462 A1 | 10/1990 |
| EP | 0638567 | 2/1995 |
| EP | 0371564 B1 | 7/1995 |
| EP | 0669919 A | 12/1995 |
| EP | 1026160 A1 | 8/2000 |
| EP | 0885190 A | 5/2003 |
| EP | 1355888 | 10/2003 |
| FR | 2436781 | 5/1980 |
| GB | 732581 A | 6/1955 |
| GB | 1062357 | 3/1967 |

(Continued)

OTHER PUBLICATIONS

Calabrese et al. Journal of the National Cancer Institute, 2004, 96(1), 56-69.*
Tentori et al. Pharmacological Research, 2005, 52, 25-33.*
"Cancer definition", http://www.medterms.com/script/main/art.asp?articlekey=2580, accessed Nov. 27, 2007.*
"Prostate Cancer Prevention", http://www.cancer.gov/cancertopics/pdq/prevention/prostate/Patient, accessed Apr. 9, 2010.*

(Continued)

*Primary Examiner* — Noble Jarrell

(57) ABSTRACT

The present invention provides compounds of formula (I), their use as PARP inhibitors as well as pharmaceutical compositions comprising said compounds of formula (I) wherein $R^1$, $R^2$, $R^3$, L, X, Y and Z have defined meanings.

(I)

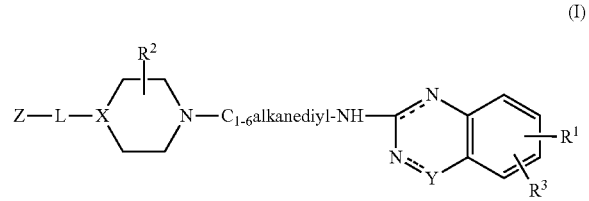

17 Claims, No Drawings

(56) References Cited

FOREIGN PATENT DOCUMENTS

| | | |
|---|---|---|
| JP | 59-076082 | 4/1984 |
| JP | 60-120872 | 6/1985 |
| JP | 60-226862 | 11/1985 |
| JP | 62-234065 | 10/1987 |
| JP | 10007572 | 1/1998 |
| JP | 10-330377 | 12/1998 |
| JP | 2002-515072 | 3/1999 |
| JP | 2000-505100 | 4/2000 |
| JP | 2000191659 | 7/2000 |
| JP | 2002-535409 | 8/2000 |
| JP | 2002284699 | 10/2002 |
| WO | 91/12006 A2 | 8/1991 |
| WO | 93/22309 A1 | 11/1993 |
| WO | 94/19342 A1 | 9/1994 |
| WO | 95/24379 | 9/1995 |
| WO | 99/11649 A2 | 3/1999 |
| WO | 99/29687 A1 | 6/1999 |
| WO | 00/44755 A1 | 8/2000 |
| WO | 02/28837 A1 | 4/2002 |
| WO | 02/36599 A1 | 5/2002 |
| WO | 03/015785 A1 | 2/2003 |
| WO | 03/039460 A2 | 5/2003 |
| WO | 03/055865 A | 7/2003 |
| WO | 03/055865 A1 | 7/2003 |
| WO | 03/080581 A1 | 10/2003 |
| WO | 03/082350 A2 | 10/2003 |
| WO | 03/101985 A1 | 12/2003 |
| WO | 2004/043950 A1 | 5/2004 |
| WO | 2005/004801 A2 | 1/2005 |
| WO | 2005/054199 A1 | 6/2005 |
| WO | 2005/054201 A1 | 6/2005 |
| WO | 2005/054209 A1 | 6/2005 |
| WO | 2005/054210 A1 | 6/2005 |
| WO | 2005/058843 A1 | 6/2005 |
| WO | 2005/097750 A1 | 10/2005 |
| WO | 2005/117876 A1 | 12/2005 |
| WO | 2006/003147 A1 | 1/2006 |
| WO | 2006/003148 A1 | 1/2006 |
| WO | 2006/003150 A1 | 1/2006 |
| WO | 2006/089177 A2 | 8/2006 |
| WO | 2007/025009 A2 | 3/2007 |
| WO | 2007/087684 A1 | 8/2007 |
| WO | 2007/095628 A1 | 8/2007 |
| WO | 2008/107478 A1 | 9/2008 |
| ZA | 72 08536 A | 11/1972 |

OTHER PUBLICATIONS

Weltin, et al., "Effect of 6(5—Phenanthridinone), an Inhibitor of Poly (ADP-ribose) Polymerase, on Cultured Tumor Cells", Oncol. Res., 6:9, 399-403 (1994).

Nguewa, et al., "Poly(ADP-Ribose) Polymerases: Homology, Structural Domains and Functions. Novel Therapeutical Applications", Progress in Biophysics & Molecular Biology 88 (2005), 143-172.

Gupta, C.M. et al., Journal of Medicinal Chemistry, vol. 11, No. 2, Feb. 26, 1968, pp. 392-395.

Hori, Manabu et al., Chemical and Pharmaceutical Bulletin, vol. 38, No. 3, Mar. 1, 1990, pp. 681-687.

Hori, Manabu et al., Chemical and Pharmaceutical Bulletin, vol. 38, No. 5, 1990, pp. 1286-1291.

Albert, J.M., et al., "Inhibition of Poly(ADP-Ribose) Polyerase Enhances Cell Death and Improves Tumor Growth Delay in Irradiated Lung Cancer MODels", Clin Cancer Res, (2007), vol. 13, No. 10, pp. 3033-3042.

Ali, M.M., et al., "Synthesis and Antimicrobial Activities of Some Novel Quinoxalinone Derivatives", Molecules, (2000), vol. 5, No. 6, pp. 864-873.

Ame, J.C., et al., "PARP-2, A Novel Mammalian DNA Damage-Dependent Poly(ADP-Ribose) Polymerase", Journal of Biological Chemistry, (1999), vol. 274, No. 25, pp. 17860-17868.

Ame, J.C., et al., "The PARP Superfamily", BioEssays, (2004), vol. 26, No. 8, pp. 882-893.

Bellasio, E., et al., "Antihypertensives. N-1H-Pyrrol-1-YL-3-Pyridazinamines", J. Med. Chem., (1984), vol. 27, No. 8 pp. 1077-1083.

Bernard et al., "Automated docking of 82 N-benzylpiperidine derivatives to mouse acetylcholinesterase and comparative molecular field analysis with 'natural' alignment.", Journal of Computer-Aided Molecular Design, 1999, 13(4), pp. 355-371.

Blackburn, W., et al., "The Preparation of 3-Methyl-6- and -7-Carboxy-2- Quinoxalones", Journal of Organic Chemistry, ((1961), vol. 26, pp. 2805-2809.

Bloch, W., et al., "Poly-Adenosine Diphosphate-Ribose Polymerase Inhibition for Myocardial Protection: Pathopysiologic and Physiologic Considerations", Journal of Thoracic and Cardiovascular Surgery, Aug. 2004, vol. 128, No. 2, pp. 323-324.

Bonne, D., et al., "4'6-Diamidino-2-phenylindole, a Fluorescent Probe for Tubulin and Microtubules", Journal of Biological Chemistry, vol. 260, No. 5 (1985) pp. 2819-2825.

Borisy et al., "Systematic Discovery of Multicomponent Therapeutics.", PNAS, Jun. 24, 2003, pp. 7977-7982, vol. 100(13).

Calabrese, C.R., et al., "Anticancer Chemosensitization and Radiosensitization by the Novel Poly(ADP-Ribose) Polymerase-1 Inhibitor AG14361", Journal of the National Cancer Institute, (2004), vol. 96, No. 1, pp. 56-67.

Cardozo, M.G., et al., "Conformational Analyses and Molecular-Shape Comparisons of a Series of Indanone-Benzylpiperidine Inhibitors of Acetylcholinesterase", J. Med. Chem., (1992), vol. 35, pp. 590-601.

CAS Registry Numbers: 464169-24-2, 464169-25-3, 223587-51-7 abstract; figure 24-&JP 2002 284699 A (Sumitomo Pharmaceuticals Co., Ltd., Japan) Oct. 3, 2002.

Cockcroft, X., et al., "Phthalazines 2: Optimisation and Synthesis of Novel Potent Inhibitors of Poly(ADP-Ribose)Polymerase", Bioorganic & Medicinal Chemistry Letters, (2006), vol. 16, pp. 1040-1044.

Costantino, G., et al., "Modeling of Poly(ADP-Ribose)Polymerase (PARP) Inhibitors. Docking of Ligands and Quantitative Structure-Activity Relationship Analysis", J. Med. Chem., (2001), vol. 44, pp. 3786-3794.

Cuzzocrea, S., "Shock Inflammation and PARP", Pharmacological Research, (2005), vol. 52, pp. 72-82.

Darchen et al., "Ketanserin binds to the monoamine transporter of chromaffin granules and of synaptic vesicles.", Molecular Pharmacology, 1988, 33(6), pp. 672-677.

Dastmalchi, S., et al., "Molecular Modelling of Human Aldehyde Oxidase and Identification of the Key Interactions in the Enzyme-Substrate Complex", Daru, J. Faculty of Pharm., (2005), vol. 13, No. 3, pp. 82-93.

Database CA Online! Chemical Abstracts Service, Columbus, Ohio, US; 2002, Tatsuno, Toru et al: "PARP Inhibitors for Treatment of Retinal Degeneration or Chemotherapy-Induced Cell Injury" XP002348719 retrieved from STN Database accession No. 2002:747681.

Database WPI Online! Derwent Publications Ltd., London, GB; XP002347462, retrieved from WPI accession No. 1970-18449R, *;see RN 27631-66-9:3-(piperidin-1-yl-propyl)-1H-quinazoline-2,4-dione*, abstract & JP 45007058B (Sankyo) Jul. 6, 1967.

Dörwald, F.Z., "Side Reactions in Organic Synthesis": A Guide to Successful Synthesis Design, Weinheim: Wiley-VCH Verlag GmbH & Co. KGaA, (2005), Preface.

EDAN30610, Jun. 8, 2011.

Finney, D. J., "Graded Response: The Linear Dosage-Response Curve", Probit Analysis, 2nd Edition, Chapter 10 (1962), Cambridge Publishing Press, 16 page article.

Golbraikh, A., et al., "Validation of Protein-Based Alignment in 3D Quantitative Structure-Activity Relationships With CoMFA Models", Eur. J. Med. Chem., (2000), vol. 35, pp. 123-136.

Guery, S., et al., "Synthesis of 4-Aryl-1-(4-Methylpiperazin-1-YL)Phthalazines by Suzuki-Type Cross-Coupling Reaction", Synthesis, (2001), No. 5, pp. 699-701.

Habon, T., et al., "The Effect of Carvedilol on Enhanced ADP-Ribosylation and Red Blood Cell Membrane Damage Caused by Free Radicals", Cardiovascular Research, (2001), vol. 52, p. 153-160.

(56) References Cited

OTHER PUBLICATIONS

Hayao, S., et al., "New Sedative and Hypotensive 3-Substituted 2,4(1 H,3h-)- Quinazolinediones", Journal of Medicinal Chemistry, (1965), vol. 8, pp. 807-811.
Hazard, P.R., et al., "De Quelques Actions Pharmacologiques Exercees Par Des Derives De L'Orthoprocainamide", Thérapie, (1965), vol. XX, pp. 1043-1049.
Herndon, J.L., et al., "Ketanserin Analogues: Structure-Affinity Relationships for 5-HT2 and 5-HT1C Serotonin Receptor Binding", J. Med. Chem., (1992), vol. 35, pp. 4903-4910.
Horvath, E.M., et al., "Poly(ADP-Ribose) Polymerase as a Drug Target for Cardiovascular Disease and Cancer: an Update", Drug News Perspect, (2007), vol. 20, No. 3, pp. 171-181.
Jordan, V.C., "Tamoxifen: A Most Unlikely Pioneering Medicine", Nature Reviews, (2003), vol. 2, pp. 205-213.
Katoh, A., et al., "Synthesis of Quinoxaline Derivatives Bearing the Styryl and Phenylethynyl Groups and Application to a Fluorescence Derivatization Reagent", Heterocycles, (2000), vol. 52, No. 2, pp. 911-920.
Kormendy, K. and Ruff, F., "Aminophthalazinone Derivatives, VII* Reaction of Chlorophthalazinone With Secondary Amines Study of the Steric Effect, II." *Acta Chimica Academiae Scientiarum Hunqaricae*, 1981, pp. 155-166, vol. 106(2).
Kormendy, K. and Ruff, F., "Aminophthalazinone Derivatives, VII. Methods for the Synthesis of Imidazo[2,1- α]Phthalazine and Pirimido[2,1- α]Phthalazine Ring Systems, I.", *Acta Chimica Hungarica*, 1983, pp. 65-82, vol. 112(1).
Kormendy, K., et al., "Aminophthalazinone Derivatives, V Synthesis of 4-Hydrazino-1-(2-H)Ophthalazinones, I", Acta Chimica Academiae Scientiarum Hungaricae, (1979), vol. 102, No. 1, pp. 39-50.
Kornet, M.J., et al., "Synthesis of 3-Amino-2,4(1 H,3H)-Quinazolinediones for Testing as Anticonvulsants", J. Heterocyclic Chem., (1984), vol. 21, No. 5, pp. 1533-1535.
Kulcsar, G., et al., Synthesis and Study of New 4-Quinazolinone Inhibitors of the DNA Repair Enzyme Poly(ADP-Ribose) Polymerase (PARP), Arkivoc, XX,XX, (2003), vol. 2003, No. Part V, pp. 121-131.
Larner, A.J., "Poly(ADP-Ribose) Polymerase Inhibitors in the Prevention of Neuronal Cell Death", Expert Opin. Ther. Patents, (2002), vol. 12, No. 4, pp. 481-487.
Leysen et al., "Non-serotonergic [$^3$ H]ketanserin binding sites in striatal membranes are associated with a dopac release system on dopaminergic nerve endings.", European Journal of Pharmacology, 1987, 134(3) 373-375.
Lord, C.J., et al., "Targeted Therapy for Cancer Using PARP Inhibitors", Current Opinion in Pharmacology, (2008), vol. 8, pp. 363-369.
Meier, H.L., et al., "Alterations in Human Lymphocyte DNA Caused by Sulfur Mustard Can Be Mitigated by Selective Inhibitors of Poly(ADP-Ribose) Polymerase", Biochimica et Biophysica Acta, (1998), vol. 1404, pp. 367-376.
Miller, B.A., "Inhibition of TRPM2 Function by PARP Inhibitors Protects Cells From Oxidative Stress-Induced Death", British Journal of Pharmacology, (2004), vol. 143, pp. 515-516.
Oliver, A.W., et al., "Crystal Structure of the Catalytic Fragment of Murine Poly(ADP-Ribose) Polymerase-2", Nucleic Acids Research, (2004), vol. 32, No. 4, pp. 456-464.
Pailer et al., "Syntheisis of quinoxalone derivatives.", Monatshefte fuer Chemie, 1962, pp. 1005-1010, vol. 93.

Patent Abstracts of Japan, vol. 1998, No. 5, Apr. 30, 1998-& JP 10007572 a (Sumitomo Pharmaceut Co Ltd), Jan. 13, 1998 '0046!, Formula 14 abstract.
Peters et al., "Basis for effective combination cancer chemotherapy with antimetabolites.", Pharmacology & Therapeutics, 2000, pp. 227-253, vol. 87.
Schreiber, V., et al., "Poly(ADP-Ribose) Polymerase-2 is Required for Efficient Base Excision DNA Repair in Association With PARP-1 and XRCC1", Journal of Biological Chemistry, (2002), vol. 277, No. 25, pp. 23028-23036.
Szabo, G., et al., "Poly(ADP-Ribose Polymerase Inhibition Protects Against Myocardial and Endothelial Reperfusion Injury After Hypothermic Cardiac Arrest", Journal of Thoracic and Cardiovascular Surgery, (2003), vol. 126, No. 3, pp. 651-658.
Takai, H., et al., "Synthesis of Piperidine Derivatives With a Quinazoline Ring System as Potential Antihypertensive Agents", Chem. Pharm. Bull, (1986), vol. 34, No. 5, pp. 1907-1916.
Tasatargil, A., et al., "Poly(ADP-Ribose) Polymerase Inhibition Prevents Homocysteine-Induced Endothelial Dysfunction in the Isolated Rat Aorta", Pharmacology, (2004), vol. 72, pp. 99-105.
Tentori, L., et al. "Poly(ADP-ribose)polymerase (PARP) Inhibition or PARP-1 gene Deletion Reduces Angiogenesis", European Journal of Cancer, vol. 43, No. 14 (2007) pp. 2124-2133.
The Merck Index, 13th Ed., p. 670, monograph for "Ethyl Alcohol" © 2001 by Merck and Co., Inc.
Vippagunta, S.R., et al., "Crystalline Solids", Advanced Drug Delivery Reviews, (2001), vol. 48, pp. 3-26.
Virag, L., et al., "The Therapeutic Potential of Poly(ADP-Ribose) Polymerase Inhibitors", Pharmacological Reviews, (2002), vol. 54, No. 3, pp. 375-429.
Weltin, D., et al., "Effect of 6(5H)-Phenanthridinone, an Inhibitor of Poly(ADP-ribose) Polymerase, on Cultured Tumor Cells", Oncology Research, (1994), vol. 6, No. 9, pp. 399-403.
Wolff, M.E., Burger's Medicinal Chemistry, 4th ed., Part I The Basis of Medicinal Chemistry, (1980), pp. 336-337.
Yolles, S., et al., "Quinoxaline Studies. I. The Preparation of 2-Hydroxy-3-Methyl-6-Methoxyquinoxaline and 2-Hydroxy-3-Methyl-7-Methoxyquinoxaline", Journal of the American Chemical Society, (1949), vol. 71, pp. 2375-2377.
Zhang, J., "PARP Inhibition: A Novel Approach to Treat Ischaemia/Reperfusion and Inflammation-Related Injuries", Emerging Drugs, (1999), vol. 4, pp. 209-221.
International Search report for Application No. PCT/EP2004/013162 mailed Mar. 18, 2005.
International Search report for Application No. PCT/EP2004/013163 mailed Apr. 20, 2005.
International Search report for Application No. PCT/EP2004/013164 mailed Mar. 14, 2005.
International Search report for Application No. PCT/EP2004/013165 mailed Mar. 24, 2005.
International Search report for Application No. PCT/EP2005/053030 mailed Oct. 24, 2005.
International Search report for Application No. PCT/EP2005/053031 mailed Oct. 25, 2005.
International Search report for Application No. PCT/EP2008/052764 mailed Aug. 12, 2008.
International Search report for Application No. PCT/EP2008/064243 mailed Mar. 30, 2009.
International Search report for Application No. PCT/EP2009/053598 mailed May 19, 2009.
International Search report for Application No. PCT/EP2009/053604 mailed May 8, 2009.

* cited by examiner

QUINAZOLINONE DERIVATIVES AS PARP INHIBITORS

CROSS REFERENCE TO RELATED APPLICATIONS

This application is the national stage of Application No PCT/EP2005/053029, filed June 28, 2005, which claims priority from EPO Patent Application No. 04076887.1 filed June 30, 2004, the entire disclosures of which are hereby incorporated in their entirely.

FIELD OF THE INVENTION

The present invention relates to inhibitors of PARP and provides compounds and compositions containing the disclosed compounds. Moreover, the present invention provides methods of using the disclosed PARP inhibitors for instance as a medicine.

BACKGROUND OF THE INVENTION

The nuclear enzyme poly(ADP-riboso) polymerase-1 (PARP-1) is a member of the PARP enzyme family. This growing family of enzymes consist of PARPs such as, for example: PARP-1, PARP-2, PARP-3 and Vault-PARP; and Tankyrases (TANKs), such as, for example: TANK-1, TANK-2 and TANK-3. PARP is also referred to as poly(adenosine 5'-diphospho-ribose) polymerase or PARS (poly (ADP-ribose) synthetase).

PARP-1 is a major nuclear protein of 116 kDa consisting of three domains: the N-terminal DNA binding domain containing two zinc fingers, the automodification domain and the C-terminal catalytic domain. It is present in almost-all eukaryotes. The enzyme synthesizes poly(ADP-ribose), a branched polymer that can consist of over 200 ADP-ribose units. The protein acceptors of poly(ADP-ribose) are directly or indirectly involved in maintaining DNA integrity. They include histones, topoisomerases, DNA and RNA polymerases, DNA ligases, and $Ca^{2+}$- and $Mg^{2+}$-dependent endonucleases. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold, Tankyrases (TANKs) were identified as components of the human telomeric complex. They have also been proposed to have a role in vesicle traffiecidng and may serve as scaffolds for proteins involved in various other cellular processes. Telomeres, which are essential for chromosome maintenance and stability, are maintained by teloinerase, a specialized reverse transcriptase. TANKs are (ADP-ribose)transferases with some features of both signalling and cytoskeletal proteins. They contain the PAR? domain, which catalyses poly-ADP-ribosylation of substrate proteins, the sterile alpha motif, which is -shared with certain signalling molecules and the ANK domain, which contains 24 ankyrin repeats homologues to the cytoskeletal protein ankyrin. The ANK domain interacts with a telomeric protein, Telomere Repeat binding Factor-1 (TRP-1). These proteins were therefore named TRF1-interacting, ankyrin-related ADP-ribose polymerase (TANKs).

One of the more specific functions of TANK is the ADP-ribosylation of TRF-1. Human telomere function requires two telomere-specific DNA binding proteins, TRF-1 and TRF-2. TRF-2 protects chromosome ends, and TRF-1 regulates telomeric length. ADP-ribosylation inhibits the ability of TRF-1 to bind to telomeric DNA. This poly-ADP-ribosylation of TRF-1 releases TRF-1 from the telomeres, opening up the telomeric complex and allow access to telomerase. Therefore, TANK functions as a positive regulator of telomere length., allowing-elongation of the telomeres by telomerase.

Among the many functions attributed to PARP, and especially PARP-1, is its major role in facilitating DNA repair by ADP-ribosylation and therefore coordinating a number of DNA repair proteins. As a result of PART activation, $NAD^+$ levels significantly decline. Extensive PARP activation leads to severe depletion of $NAD^+$ in cells suffering from massive DNA damage. The short half-life of poly(ADP-ribose) results in a rapid turnover rate. Once poly(ADP-ribose) is formed, it is quicldy degraded by the constitutively active poly(ADP-ribose) glycohydrolase (PARG), together with phosphodiesterase and (ADP-ribose) protein lyase. PARP and PARG form a cycle that converts a large amount off ADP to ADP-ribose. In less than an hour, over-stimulation of PARP can cause a drop of $NAD^+$ and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to $NAD^+$ depletion due to poly(ADP-ribose) turnover. Thus, PART or PARG inhibition is expected to preserve the cellular energy level thereby potentiating the survival of ischaemic tissues after insult Poly(ADP-ribose) synthesis is also involved in the induced expression of a number of genes essential.for inflammatory response. PARP inhibitors suppress production of inducible nitric oxide syntbase (iNOS) in rnacrophages, P-type selectin and intercellular adhesion molecule-1 (ICAM-1) in endothelial cells. Such activity underlies the strong anti-inlamnmation effects exhibited by PARP inhibitors. PARP inhibition is able to reduce necrosis by preventing translocation and infiltration of neutrophils to the injured tissues.

PARP is activated by damaged DNA fragments and, once activated, catalyzes the attachment of up to 100 ADP-ribose units to a variety of nuclear proteins, including histones and PARP itself. During major cellular stresses the extensive activation of PARP can rapidly lead to cell damage or death through depletion of energy stores. As four molecules of ATP are consumed for every molecule of $NAD^+$ regenerated, $NAD^+$ is depleted by massive PARP activation, in the efforts to re-synthesize $NAD^+$, ATP may also become depleted.

It has been reported that PAR-P activation plays a key role in both NMDA- and NO-induced neurotoxicity. This has been demonstrated in cortical cultures and in hippocampal slices wherein prevention of toxicity is directly correlated to PARP ilnhibition potency. The potential role of PARP inhibitors in treating neurodegenerative diseases and head trauma has thus been recognized even if the exact mechanism of action has not yet been elucidated.

Similarly, it has been demonstrated that single injections of PARP inhibitors have reduced the infarct size caused by iscbemia and reperfusion of the heart or skeletal muscle in rabbits. In these studies, a single injection of 3-amino-benzamide (10 mg/kg), either one minute before occlusion or one minute before reprrfusion, caused similar reductions in infarct size in the heart (32-42%) while 1,5-dihydroxyisoquinoline (1 mg/kg), another PARP inhibitor, reduced infarct size by a comparable degree (38-48%. These results make it reasonable to assume that PARP inhibitors could salvage previously ischaemic heart or reperfusion injury of skeletal muscle tissue.

PARP activation can also be used as a measure of damage following neurotoxic insults resulting from exposure to any of the following inducers like glutamate (via NMDA receptor stimulation), reactive oxygen intermediates, amyloid β-protein, N-methyl-4-phenyl-1,2,3,6-tetrahydropyridine (MPTP) or its active metabolite N-methyl-4-phenylpyridine (MPP$^+$), which participate in pathological conditions such as stroke, Alzbeimer's disease and Parkinsones disease. Other studies have continued to explore the role of PARP activation in cerebellar granule cells in vitro and in MPTP neurotoxicity. Excessive neural exposure to glutamate, which serves as the predominate central nervous system neurotransmitter and acts upon the N-methyl D-aspartate NMDA) receptors and other subtype receptors, most often occurs as a result of stroke or other neurodegenerative processes. Oxygen deprived neurons release glutamate in great quantities during ischaemic brain insult such as during a stroke or heart attack. This excess release of glutamate in turn causes over-stimulation (excitotoxicity) of N-methyl-D-aspartate MA), AMPA, Kainate and MGR receptors, which open ion channels and permit uncontrolled ion flow (e.g., $Ca^{2+}$ and $Na^+$ into the cells and $K^+$ out of the cells) leading to overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult Glutamate exposure and stimulation has also been implicated as a basis for compulsive disorders, particularly drug dependence. Evidence includes findings in many animal species, as well as in cerebral cortical cultures treated with glutamate or NPDA, that glutamate receptor antagonists (i.e., compounds which block glutamate from binding to or activating its receptor) block neural damage following vascular stroke. Attempts to prevent excitotoxicity by blocking NMDA, AMPA, Kainate and MGR receptors have proven difficult because each receptor has multiple sites to which glutamate may bind and hence finding an effective mix of antagonists or universal antagonist to prevent binding of glutamate to all of the receptor and allow testing of Iisi theory, has been difficult Moreover, many of the compositions that are effective in blocldng the receptors are alsoyoxic to animals. As such, there is presently no known effective treatment for glutamate abnormalities.

The stimulation of NMDA receptors by glutamate, for example, activates the enzyme neuronal nitric oxide synthase (nNOS), leading to the formation of nitric oxide (NO), which also mediates neurotoxicity. NMDA neurotoxicity may be prevented by treatment with nitric oxide synthase (NOS) inhibitors or through targeted genetic disruption of nNOS in vitro.

Another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs.

Evidence also exists that PARP inhibitors are useful for treating inflammatory bowel disorders, such as colitis. Specifically, colitis was induced in rats by intraluminal administration of the hapten trinitrobenzene sulfonic acid in 50% ethanol. Treated rats received 3-aminobenzanmide, a specific inhibitor of PARP activity. Inhibition of PARP activity reduced the inflammatory response and restored the morphology and the energetic status of the distal colon.

Further evidence suggests that PARP inhibitors are useful for treating arthritis. Further, PARP inhibitors appear to be useful for treating diabetes. PARP inhibitors have been shown to be useful for treating endotoxic shock or septic shock.

PARP inhibitors have also been used to extend the lifespan and proliferative capacity of cells including treatment of diseases such as skin aging, Alzheimer's disease, atherosclerosis, osteoarrtis, osteoporosis, muscular dystrophy, degenerative diseases of skeletal muscle involving replicative senescence, age-related muscular degeneration, immune senescence, AIDS, and other immune senescence disease, and to alter gene expression of senescent cells.

It is also known that PARP inhibitors, such as 3-amino benzamide, affect overall DNA repair in response, for example, to hydrogen peroxide or ionizing radiation.

The pivotal role of PARP in the repair of DNA strand breaks is well established, especially when caused directly by ionizing radiation or, indirectly after enzymatic repair of DNA lesions inauced by methylating agents, topoisomerases I inhibitors and other chemotherapeutic agents as cisplatin and bleomycin. A variety of studies using "knockout" nice, trans-dominant inhibition models (over-expression of the DNA-binding domain), antisense and small molecular weight inhibitors have demonstrated the role of PAPRP in repair and cell survival after induction of DNA damage. The inhibition of PARP enzymatic activity should lead to an enhanced sensitivity of the tumor cells towards DNA damaging treatments.

PARP inhibitors have been reported to be effective in radiosensitizing (hypoxic) tumor cells and effective in preventing tumor cells from recovering from potentially lethal and sublethal damage of DNA after radiation therapy, presumably by their ability to prevent DNA strand break rejoining and by affecting several DNA damage signaling pathways.

PARP inhibitors have been used to treat cancer. In addition, U.S. Pat. No. 5,177,075 discusses several isoquinolines used for enhancing the lethal effects of ionizing radiation or chemotherapeutic agents on tumor cells. Weltin et al., "effect of 6(5-Phenanthridinone), an Inhibitor of Poly(ADP-ribose) Polymerase, on Cultured Tumor Cells", Oncol. Res., 6:9,399-403 (1994), discusses the inhibition of PARP activity, reduced proliferation of tumor cells, and a marked synergistic effect when tumor cells are co-treated with an alkylating drug.

Reviews of te state of the art has been published by Li and Zhang in IDrugs 2001, 4(7): 804-812, by Ame et al in Bioassays 2004, 26: 882-883 and by Nguewa et al., in Progress in Biophysic & Molecular Biology 2005, 88: 143-172.

There continues to be a need for effective and potent PARP inhibitors, and more particularly PARP-1 inhibitors which produce minimal side effects. The present invention provides compounds, compositions for, and methods of, inhibiting PARP activity for treating cancer and/or preventing cellular, tissue andlor organ damage resulting from cell damage or death due to, for example, necrosis or apoptosis. The compounds and compositions of the present invention are especially useful in enhancing the effectiveness of chemotherapy and radiotherapy where a primary effect of the treatment is that of causing DNA damage in the targeted cells.

BACKGROUND PRIOR ART

GB 1062357 published on Mar. 22, 1967 discloses quinazolone derivatives having antihypertensive effects.

DE 2258561 published on Jun. 20, 1973 discloses substituted pyridinone derivatives with antihypertensive action.

EP 13612, published on Nov. 11, 1983, discloses substituted pipexidinylalkylquinazoline derivatives. The described compounds are serotonin-antagonists.

EP 669919, published on Jun. 9, 1994, discloses dimethylbenzofurans and dimethylbenzopyrans as 5-HT$_3$ antagonists. More in particular compounds No. 8, 4, 5, 10, 11, 12, 13, 15, 16, 17 and 14 of the present application are disclosed. U.S. Pat. No. 5,374,637, published on Dec. 20, 1994, discloses benzamide derivatives. The disclosed compounds have gastrointestinal motility stimulating propres. In particular compounds No. 8, 6 and 9 of the present application are disclosed. EP 885190, published on Dec. 23, 1998 discloses 1,4-disubstituted piperidine derivatives having gastrokinetic properties. In particular compound No. 7 of the present application is disclosed.

EP 1036073, published on Jun. 17, 1999, discloses substituted quinazolinedione derivatives. The described compounds have fundic relaxation properties.

HP 1355888 published on 20 Jun. 2002 discloses quinazolinone derivatives as PARP inhibitors.

DESCRIPTION OF THE INVENTION

This invention concerns compounds of formula (I)

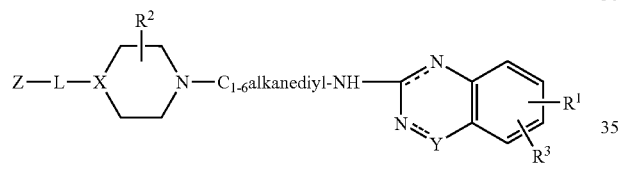
(I)

the N-oxide forms, the pharmaceutically acceptable addition salts and the stereo-chemically isomeric forms thereof, wherein the dotted lines represent optional bonds;

X is >N— or >CH—;

—N══Y— is —N—C(O)— or —N═CR$^4$—, wherein R$^4$ is hydroxy;

L is a direct bond or a bivalent radical selected from —C(O)—, —C(O)—NH—, —NH—, —C(O)—C$_{1-6}$alkanediyl-, —C(O)—O—C$_{1-6}$alkanediyl- or —C$_{1-6}$alkanediyl-;

R$^1$ is hydrogen, halo, C$_{1-6}$alkyloxy or C$_{1-6}$alkyl;

R$^2$ is hydrogen, hydroxy, C$_{1-6}$alkyloxy or aminocarbonyl; when X is substituted with R$^2$ than R$^2$ taken together with -L-Z can form a bivalent radical of formula —C(O)—NH—CH$_2$—NR$^{10}$— 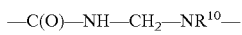 (a-1)

wherein R$^{10}$ is phenyl;

R$^3$ is hydrogen, or C$_{1-6}$alkyloxy;

Z is amino, cyano or a radical selected from

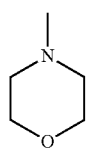
(b-1)

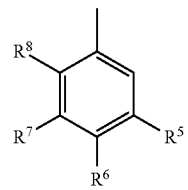
(b-2)

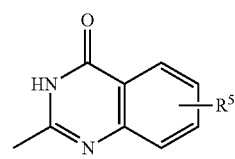
(b-3)

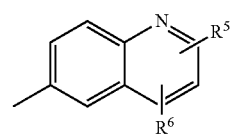
(b-4)

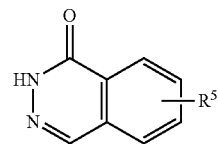
(b-5)

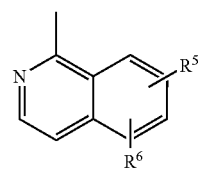
(b-6)

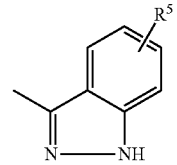
(b-7)

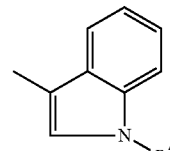
(b-8)

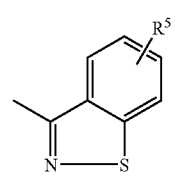
(b-9)

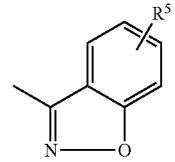
(b-10)

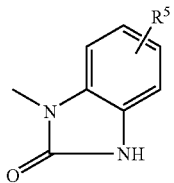 (b-11)

wherein each $R^5$, $R^6$, $R^7$ and $R^8$ is independently selected from hydrogen, halo, amino, $C_{1-6}$alkyl or $C_{1-6}$alkyloxy; or $R^7$ and $R^8$ taken together may form a bivalent radical of formula —CH$_2$—CR$^9_2$—O— (c-1), —(CH$_2$)$_3$—O— (c-2), —O—(CH$_2$)$_2$—O— (c-3) or —CH═CH—CH═CH— (c-4)

wherein each $R^9$ is independently selected from hydrogen or $C_{1-6}$alkyl;

with the proviso that when X is >N—, then Z is other than the radical (b-2) and when X is >CH— and L is —C(O)—NH— or —C(O)—O—$C_{1-6}$alkanediyl- and Z is the radical (b-2) and $R^7$ and $R^8$ taken together form a bivalent radical of formula (c-1), (c-2) or (c-3) then $R^5$ is other than chloro.

The compounds of formula (I) may also exist in their tautomeric forms. Such forms although not explicitly indicated in the above formula am intended to be included within the scope of the present invention.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methyipropyl, 2-methyl-butyl, 2-methylpentyl and the like; $C_{1-6}$alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as bydrohalic acids, e.g. hydrochloric or hydrobroniic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabanine salts, and salts with amino acids such as, for example, arginine, lysine and the like.

The terms acid or base addition salt also comprise the hydrates and the solvent addition forms which the compounds of formula (1) are able to form Examples of such forms ame e.g. hydrates, alcoholates and the like.

The term stereochemically isomenc forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine- or piperazine nitrogens are N-oxidized.

Whenever used hereinafter, the term "compounds of formula (I)" is meant to include also the N-oxide forms, the phamaceutically acceptable acid or base addition salts and all stereoisomeric forms.

GB 1062357 discloses quinazolone derivatives having antihypertensive effects. DE 2258561 discloses substituted pyridinone derivatives with antihypertensive action. EP 13612 discloses substituted piperidinylalkylquinazoline derivatives that are serotonin-antagonists. EP 669919 discloses dimethylbenzofurans and dimethylbenzopyrans as 5-HT$_3$ antagonists. U.S. Pat. No. 5,374,637 discloses benzamide derivatives that have gastrointestinal motility stimulating properties. EP 885190 discloses 1,4-disubstituted piperidine derivatives having gastrokinetic properties. EP 1036073 discloses substituted quinazolinedione derivatives that have fundic relaxation properties.

Unexpectedly, it has been found that the compounds of the present invention show PARP inhibitory activity.

A first group of interesting compounds consists of those compounds of formula (I) wherein one or more of the following restrictions apply:
a) each X is >N—;
b) L is a bivalent radical selected from —C(O)—, —C(O)—NH—, —NH—, —C(O)—$C_{1-6}$alkanediyl-, —C(O)—O—$C_{1-6}$alkanediyl- or —$C_{1-6}$alkanediyl-;
c) $R^1$ is hydrogen;
d) $R^2$ is hydroxy, $C_{1-6}$alkyloxy or aminocarbonyl;
e) Z is amino, cyano or a radical selected from (b-1), (b-3), (b-4), (b-5), (b-6), (b-7), (b-8) or (b-9);
f) each $R^5$ and $R^6$ is independently selected from hydrogen or amino.

A second group of interesting compounds consists of those compounds of formula (I) wherein one or more of the following restrictions apply:

a) X is >CH—;
b) L is a direct bond or a bivalent radical selected from —C(O)—, —NH—, —C(O)—$C_{1-6}$alkanediyl-, or —$C_{1-6}$alkanlediyl-;
c) Z is amino, cyano or a radical selected from (b-1), (b-3), (b-4), (b-5), (b-6), (b-7), (b-8) or (b-9);
d) each $R^5$ is independently selected from hydrogen, fluoro, iodo, bromo, amino, $C_{1-6}$alkyl or $C_{1-6}$alkyloxy;
e) each $R^6$ is independently selected from hydrogen, chloro, iodo, bromo, amino, $C_{1-6}$alkyl or $C_{1-6}$alkyloxy;

A third group of interesting compounds consists of those compounds of formula (I) wherein one or more of the following restrictions apply:
a) L is a direct bond or a bivalent radical selected from —C(O)—, or —C(O)—NH—;
b) $R^2$ is hydrogen, hydroxy, or $C_{1-6}$aikyloxy;
c) Z is a radical selected from (b-2), (b-3), (b-4), (b-5), (b-6), (b-7), (b-8) or (b-9);
d) each $R^5$, $R^6$, $R^7$ and $R^9$ is independently selected from hydrogen, halo, $C_{1-6}$alkyl or $C_{1-6}$alkyloxy; or
e) $R^7$ and $R^8$ taken together may form a bivalent radical of formula (c-1), or (c-4).

A fourth group of interesting compounds consists of those compounds of formula (I) wherein one or more of the following restrictions apply:
a) L is a direct bond or a bivalent radical selected from —C(O)—, or —C(O)—NH—, or —C(O)—O—$C_{1-6}$alkanediyl-;
b) $R^2$ is hydrogen, hydroxy, or $C_{1-6}$alkyloxy;
c) Z is a radical selected from (b-2), (b-3), (b-4), (b-5), (b-6), (b-7), (b-8) or (b-9);
d) each $R^5$, $R^6$, $R^7$ and $R^9$ is independently selected from hydrogen, halo, $C_{1-6}$alkyl or $C_{1-6}$alkyloxy; or
e) $R^7$ and $R^8$ taken together may form a bivalent radical of formula (c-1), (c-2), (c-3) or (c-4).

A fifth group of interesting compounds consists of those compounds of formula (I) wherein one or more of the following restrictions apply:
a) L is a direct bond;
b) $R^1$ is hydrogen, halo or $C_{1-6}$alkyl;
c) $R^2$ is hydrogen;
d) $R^3$ is hydrogen;
e) Z is a radical selected from (b-5) or (b-7);
f) each $R^5$ is independently selected from hydrogen or halo.

A group of preferred compounds consists of those compounds of formula (I) wherein L is a direct bond or a bivalent radical selected from —C(O)—, —C(O)—NH—, or —C(O)—O—$C_{1-6}$alkanediyl-; $R^2$ is hydrogen, hydroxy, or $C_{1-6}$-alkyloxy; Z is a radical selected from (b-2), (b-3), (b-4), (b-5), (b-6), (b-7), (b-8) or (b-9); each $R^5$, $R^6$, $R^7$ and $R^8$ is independently selected from hydrogen, halo, amrino, $C_{1-6}$alkyl or $C_{1-6}$alkyloxy; or $R^7$ and $R^8$ taken together may form a bivalent radical of formula (c-1), (c-2), (c-3) or (c4).

A group of more preferred compounds consists of those compounds of formula (I) wherein L is a direct bond, $R^1$ is hydrogen, halo or $C_{1-6}$alkyl;

$R^2$ is hydrogen; $R^3$ is hydrogen; Z is a radical selected from (b-5) or (b-7); and each $R^5$ is independently selected from hydrogen or halo.

The most preferred compounds are compounds No. 35, No. 36, No. 39, No. 1 and No. 43.

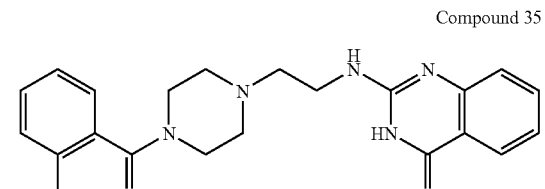
Compound 35

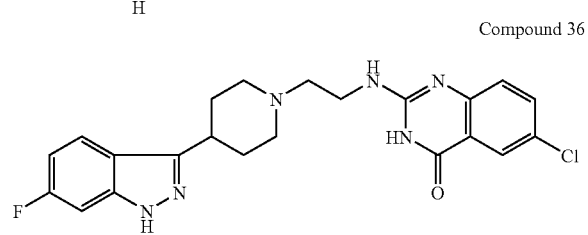
Compound 36

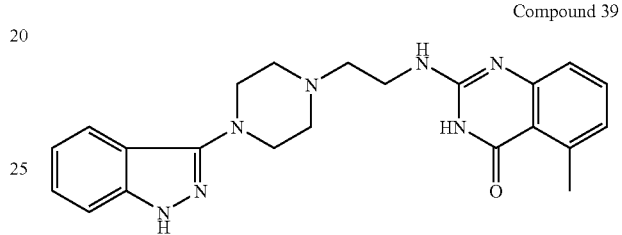
Compound 39

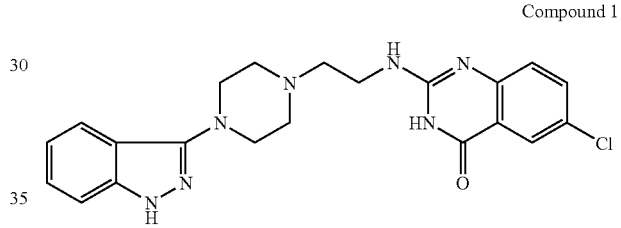
Compound 1

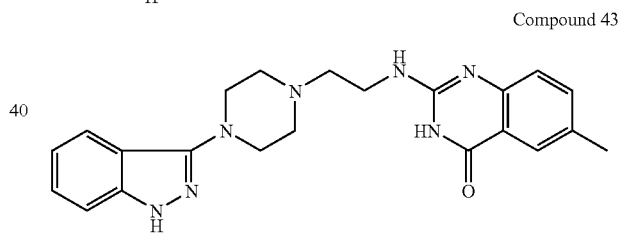
Compound 43

The compounds of formula (I) can be prepared according to the general methods described in EP 1036073, BP 885190, U.S. Pat. No. 5,374,637, EP 669919 and EP13612. The starting materials and some of the intermediates are known compounds and are commercially available or may be prepared according to conventional reaction procedures generally known in the art.

Some preparation methods will be described hereinafter in more detail. Other methods for obtaining final compounds of formula (I) are described in the examples.

The compounds of formula (I), can be prepared by reacting an intermediate of formula (II), with an intermediate of formula (III), wherein W is an appropriate leaving group such as, for example, halo, e.g. fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g. methanol, ethanol, 2-methoxy-ethanol, propanol, butanol and the like; an ether, e.g. 4, 4-dioxane, 1,1'-oxybispropane and the like; or a ketone, e.g. 4-methyl-2-pentanone, N,N-dimethylformamide, nitrobenzene and the like. The addition of an appropriate base such as, for example, an alkali or earth alkaline metal carbonate or hydrogen carbonate, e.g. triethylamine or sodium carbonate, may be utilized to pick up the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

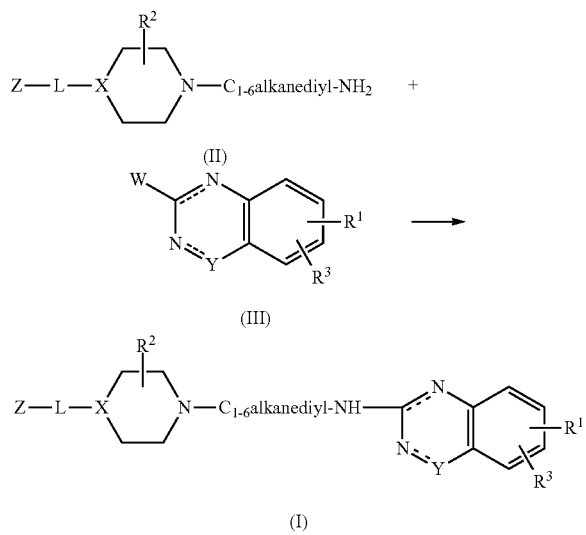

The compounds of formula (I) may also be converted into each other via art-known reactions or functional group transformations. Some of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on irnidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The present invention also relates to a compound of formula (I) as defined above for use as a medicine.

The compounds of the present invention have PARP inhibiting properties as can be seen from the experimental part hereinunder.

The term "PARP" is used herein to mean a protein having poly-ADP-ribosylation activity. Within the meaning of this term, PARP encompass all proteins encoded by a parp gene, mutants thereof, and alternative slice proteins thereof. Additionally, as used herein, the term "PARP" includes PARP analogues, homologues and analogues of other animals.

The term "PARP", includes but is not limited to PARP-1. Within the meaning of this term PARP-2, PARP-3, Vault-PARP (PARP-4), PARP-7 (TiPARP), PARP-8, PARP-9 (Bal), PARP-10, PARP-11, PARP-12, PARP-13, PARP-14, PARP-15, PARP-16, TANK-1, TANK-2, and TANK-3 may be encompassed.

Compounds that inhibit both PARP-1 and- tankyrase 2 can have advantageous properties in that they have enhanced growth inhibiting activities in cancer cells.

The present invention also contemplates the use of compounds in the preparation of a medicament for the treatment of any of the diseases and disorders in an animal described herein, wherein said compounds are compounds of formula (I)

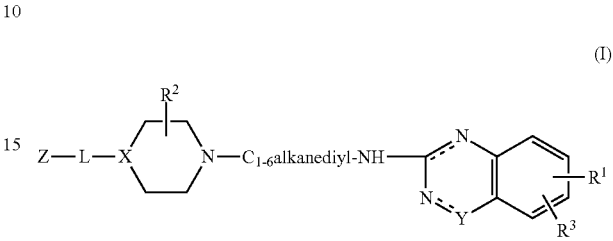

the N-oxide forms, the pharmaceutically acceptable addition salts and the stereo-chemically isomeric forms thereof, wherein the dotted lines represent optional bonds;

X is >N— or >CH—;

—N═══Y— is —N—C(O)— or —N═CR$^4$—, wherein R$^4$ is hydroxy;

L is a direct bond or a bivalent radical selected from —C(O)—, —C(O)—NH—, —NH—, —C(O)—C$_{1-6}$alkanediyl-, —C(O)—O—C$_{1-6}$alkanediyl- or —C$_{1-6}$alkanediyl-;

R$^1$ is hydrogen, halo, C$_{1-6}$alkyloxy or C$_{1-6}$alkyl;

R$^2$ is hydrogen, hydroxy, C$_{1-6}$alkyloxy or aminocarbonyl;

when X is substituted with R$^2$ than R$^2$ taken together with -L-Z can form a bivalent radical of formula $$—C(O)—NH—CH_2—NR^{10}—$$ (a-1)

wherein R$^{10}$ is phenyl;

R$^3$ is hydrogen, or C$_{1-6}$alkyloxy;

Z is amino, cyano or a radical selected from

(b-1)

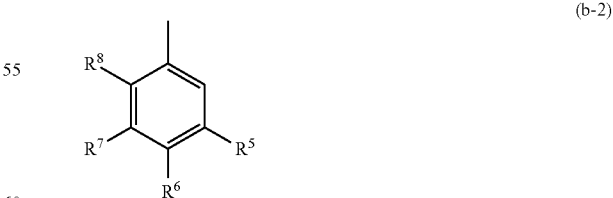

(b-2)

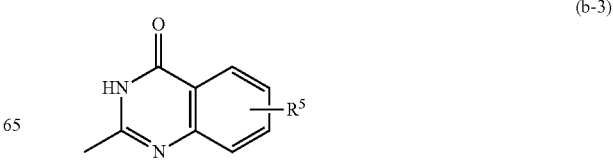

(b-3)

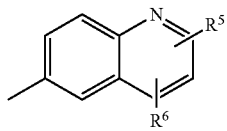 (b-4)

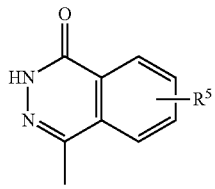 (b-5)

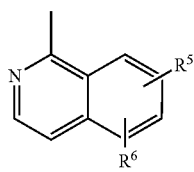 (b-6)

 (b-7)

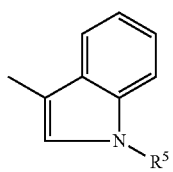 (b-8)

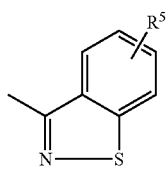 (b-9)

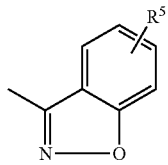 (b-10)

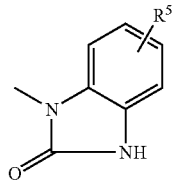 (b-11)

wherein each $R^5$, $R^6$, $R^7$ and $R^8$ is independently selected from hydrogen, halo, amino, $C_{1-6}$alkyl or $C_{1-6}$alkyloxy; or $R^7$ and $R^8$ taken together may form a bivalent radical of formula $$—CH_2—CR^9{}_2—O— \qquad (c\text{-}1),$$

$$—(CH_2)_3—O— \qquad (c\text{-}2),$$

$$—O—(CH_2)_2—O— \qquad (c\text{-}3) \text{ or}$$

$$—CH=CH—CH=CH— \qquad (c\text{-}4)$$

wherein each $R^9$ is independently selected from hydrogen or $C_{1-6}$alkyl.

Furthermore, the invention also concerns the use of a compound as described above for the manufacture of a medicament for the treatment of a disorder mediated through PARP.

In particular, the invention concerns the use of a compound as described above for the manufacture of a medicament for the treatment of a disorder mediated through PARP.

Compounds that inhibit both PARP-1 and TANK-2 can have advantages properties in that they have enhanced growth inhibiting activities in cancer cells.

In view of their PARP binding properties the compounds of the present invention may be used as reference compounds or tracer compounds in which case one of the atoms of the molecule may be replaced with, for instance, a radioactive isotope.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of ine usual pharmaceutical media may be employed, such as, for example, tater, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be include& Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the slin andlor may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention can treat or prevent tissue damage resulting from cell damage or death due to necrosis or apoptosis; can ameliorate neural or cardiovascular tissue damage, including that following focal ischernia, myocardial infarction, and reperfusion injury; can treat various diseases and conditions caused or exacerbated by PARP activity; can extend or increase the lifespan or proliferative capacity of cells; can alter the gene expression of senescent cells; can radiosensitize and/or chemosensitize cells. Generally, inhibition of PARP activity spares the cells from energy loss, preventing, in the case of neural cells, irreversible depolarization of the neurons, and thus, provides neuroprotection.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NODA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age- related muscular degeneration, AIIDS and other immune senescence diseases, inflammation, gout, arthritis, atherosclerosis, cachexia, cancer, degenerative diseases of skeletal muscle involving replicative senescence, diabetes, head trauma, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and slin aging, to extend the lifespan and proliferative capacity of cells; to alter gene expression of senescent cells; chemosensitize and/or radiosensitize (hypoxic) tumor cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. The neurological disorder is selected from the group consisting of peripheral neuropathy caused by physical injury or disease state, traumatic brain injury, physical damage to the spinal cord, stroke associated with brain damage, focal ischernia, global ischemia, reperfusion injury, demyelinating disease and neurological disorder relating to neurodegeneration.

The present invention also contemplates the use of compounds of formula (I) for inhibiting PARP activity, for treating, preventing or inhibiting tissue damage resulting from cell damage or death due to necrosis or apoptosis, for treating, preventing or inhibiting a neurological disorder in an animal.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, ie., arresting its development; (iii) relieving the disease andlor condition, i.e., causing regression of the disease and/or condition.

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation. Diseases which are treatable with ionizing radiation include neoplastic diseases, benign and malignant tumors, and cancerous cells. Ionizing radiation treatment of other diseases not listed herein are also contemplated by the present invention.

The term "chemosensitize", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics. Diseases which are treatable with chemotherapy include neoplastic diseases, benign and malignant tmors and cancerous cells. Chemotherapy treatment of other diseases not listed herein are also contemplated by the present invention.

The compounds, compositions and methods of the present invention are particularly useful for treating or preventing tissue damage resulting from cell death or damage due to necrosis or apoptosis.

The compounds of the present invention can be "anti-cancer agents", which term also encompasses "anti-tumor cell growth agents" and "anti-neoplastic agents". For example, the methods of the invention are useful for treating cancers and chemosensitizing and/or radiosensitizing tumor cells in cancers such as ACTTI-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma gallbladder cancer, hairy cell leukemia, head &neck cancer, Hodgkin's lymphoma, Kaposi's sarcoma, kidney cancer, liver cancer, lung cancer (small and/or non-small cell), malignant peritoneal eff-sion, malignant pleural effusion, melanoma, mesothelioma, multiple myeloma, neuroblastoma, non- Hodjkin's lymphoma, osteosarcoma, ovarian cancer, ovary (germ cell) cancer, prostate cancer, pancreatic cancer, penile cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva and Wilm's tumor.

Hence the compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers ( e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease. Many cancer treatment protocols currently employ radiosensitizers in conjunction with radiation of x-rays. Examples of xray activated radiosensitizers include, but are not imrited to, the following: metronidazole, misonidazole, desmethyhisonidazole, pimonidazole, etanidazole, nimorazole, mitomycin C, RSU 1069, SR 4233, EO9, RB 6145, nicotinamide, 5-bromodeoxyuridine BUdR), 5-iododeoxyuridine (IUdR), bromodeoxycytidine, fluorodeoxyuxidine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthaloayanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perrfuorocarbons (egg., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamna), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemothearpeutic agents which act on the thmor or other therapeutically effective compounds for treating cancer or other disease. Examples of additional therapeutical agents that may be used in conjunction with chemosensitizers include, but are not limited to: methylating agents, toposisomerase I inhibitors and other chemotherapeutic agents such as cisplatin and bleomycin.

The compounds of formula (I) can also be used to detect or identify the PARP, and more in particular the PARP-1 receptor For that purpose the compounds of formula (I) can be labeled. Said label can be selected from the group consisting of a radioisotope, spin label, antigen label, enzyme label fluorescent group or a chemiluminiscent group.

Those skilled in the art could easily determine the effective amount from the test results presented hereinafter. In general it is contemplated that an effective amount would be from 0.001 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage for m Experimental Part Hereinafter, "DCM" is defined as dichloromethane, "DMF" is defined as N,N-dimethylfonnannde, "MeOH" is defined as methanol, "MIK" is defined as methyl isobutyl keton, "MEK" is defined as methyl ethyl keton, "TEA" is defined as triethylamine and "THF" is defined as tetrahydrofuran.

A. Preparation of the Intermediate Compounds

EXAMPLE A1 a) Preparation of Intermediate 1

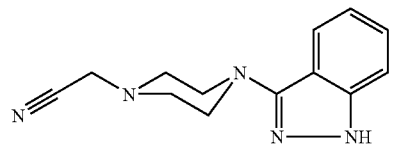 [SMILES: N#CCN1CCN(c2n[nH]c3ccccc23)CC1]

A mixture of 3-(1-piperazinyl)-1H-indazole (0.11 mol), chloro-acetonitrile (0.16 mol) and TEA (13 g) in toluene (200 ml) and acetonitile (200 ml) was stirred and refluxed for 3 hours. The cooled reaction mixture was washed with water (250 ml). The organic layer was separated, dried (MgSO$_4$), filtered and the solvent was evaporated. The residue was dissolved in trichloromethane and purified over silica on a glass filter (eluent: trichloromethane /MeOH 90/10). The purest fraction was collected and the solvent was evaporated. The residue was crystallized from acetonitrile. The crystals were filtered off and dried, yielding 26 g (99%) of intermediate 1, melting point 136° C.

b) Preparation of Intermediate 2

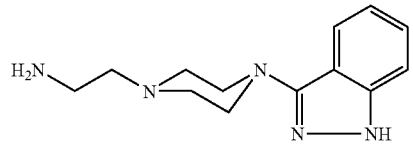 [SMILES: NCCN1CCN(c2n[nH]c3ccccc23)CC1]

A mixture of intermediate 1 (0.11 mol) in NH$_3$/MeOH (600 ml) was hydrogenated at 50° C. with Raney Nickel (4 g) as a catalyst. After uptake of H$_2$ (2 eq), the catalyst was filtered off and the filtrate was evaporated. The residue was crystallized from acetontrile. The crystals were filtered off and dried, yielding 21 g (77.5%) of intermediate 2, melting point 121° C.

EXAMPLE A2 a) Preparation of Intermediate 3

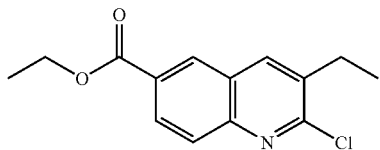 [SMILES: CCOC(=O)c1ccc2nc(Cl)c(CC)cc2c1]

Phosphoryl chloride (110.9 ml) was added dropwise at 5° C. to DMF (81.5 ml). The mixture was stirred until complete dissolution. 4[(1-oxobutyl)amino]-benzoic acid, ethyl ester (0.34 mol) was added. The mnixture was stired at 100° C. for 15 hours, then cooled to room temperature and poured out into ice water. The precipitate was filtered off, washed with water and dried, yielding 42.35 g (47%) of intermediate 3.

b) Preparation of Intermediate 4

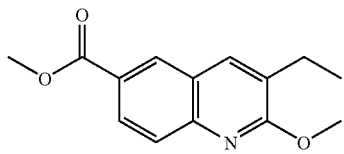

A mixture of intermediate 3 (0.1606 mol) in sodium methylate, 30% solution in MeOH (152.8 ml) and MeOH (400 ml) was stirred and refluxed for 15 hours, then cooled and poured out into ice water. The precipitate was filtered off, washed with water and taken up in DCM. The organic layer was separated, dried ($MgSO_4$), filtered and the solvent was evaporated till dryness, yielding 31.64 g (85%) of intermediate 4.

c) Preparation of Intermediate 5

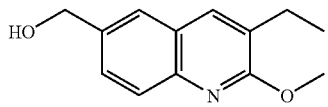 [SMILES: CCc1cc2cc(CO)ccc2nc1OC]

Lithium tetrahydroaluminate (0.1288 mol) was added portionwise at 0° C. under $N_2$ flow to a solution of intermediate 4 (0.1288 mol) in BT (263 ml). The mixture was stired for 30 min, poured out into ice water and extracted with DCM. The organic layer was separated, dried ($MgSO_4$), filtered and the solvent was evaporated till dryness, yielding 27.4 g (98%) of intermediate 5.

d) Preparation of Intermediate 6

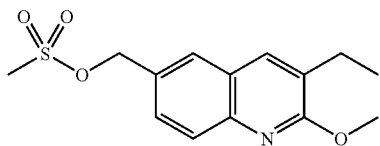

Methanesulfonyl chloride (0.104 mol) was added dropwise at 0° C. under $N_2$ flow to a mixture of intermediate 5 (0.069 mol) and TEA (0.207 mol) in DCM (120 ml). The mixture was stirred at 0° C. for 4 hours. The solvent was evaporated till dryness (without heating). The product was used without further purification, yielding 20.4 g of intermediate 6.

EXAMPLE A3 a) Preparation of Intermediate 7

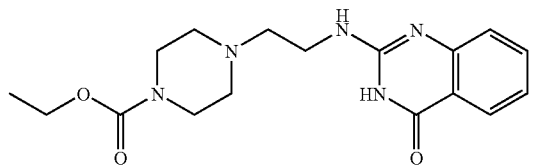 [SMILES: CCOC(=O)N1CCN(CCNc2nc3ccccc3c(=O)[nH]2)CC1]

4(2-aminoethyl)-1-piperazinecarboxylic acid, ethyl ester (0.0586 mol) and 2-(methylthio)-4(1H)-quinazolinone (0.0588 mol) were heated at 180° C. for 2 hours while stirring upon treatment with javelle water and then taken up in DCM and MeOH. The solvent was evaporated till dryness. The residue was purified by column chromatography over silica gel (15-35 μm) (eluent: DCM/MeOH/$NH_4OH$ 94/6/0.5). The pure fractions were collected and the solvent was evaporated. The oily residue was crystallized from diethyl ether. The precipitate, was filtered off and dried, yielding intermediate 7, melting point: 138° C.

b) Preparation of Intermediate 8

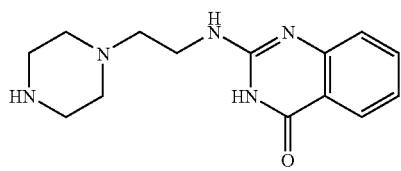 [SMILES: O=c1[nH]c(NCCN2CCNCC2)nc2ccccc12]

A mixture of intermediate 7 (0.0223 mol) and potassium hydroxide (0.223 mol) in 2-propanol (100 ml) was stirred and refluxed for 4 days. The solvent was evaporated till dryness. The residue was taken up in MeOR while stirng at 60° C. The salts were filtered off. The solvent was evaporated, yielding 6.5 g of intermediate 8.

B. Preparation of the Final Compounds

EXAMPLE B1

Preparation of Compound 1

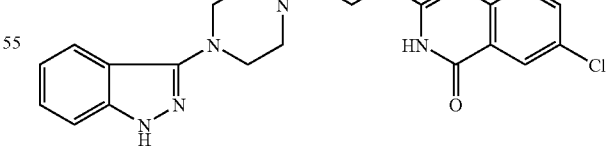

Intermediate 2 (0.000815 mol) and 6-chloro-2-(methylthio)- 4(1H)-quinazolinone (0.00097 mol) were heated at 160° C. for 1 hour, then taken up in water and potassium carbonate 10% and extracted with DCM/MeOH 90/10. The organic layer was separated, dried ($MgSO_4$), filtered and the solvent was evaporated. The residue (0.3 g) was purified by column chromatography over silica gel (15-40 μm) (eluent:

DCM/MeOH/NH₄OH 92/8/0.5). The pure fractions were collected and the solvent was evaporated. The residue was crystallized from MEK and DIPE. The precipitate was filtered off and dried, yielding 0.2 g (58%) of compound 1, melting point 186° C.

EXAMPLE B2

Preparation of Compound 2

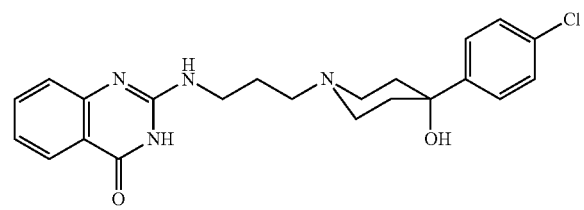 [SMILES: O=c1[nH]c(NCCCN2CCC(O)(c3ccc(Cl)cc3)CC2)nc2ccccc12]

A mixture of 1-(3-aminopropyl)-4-(4-chlorophenyl)-4-piperidinol (0.015 mol) and 2-chloro-4(1H)-quinazolinone (0.018 mol) in dimethylacetamiide (5 ml) was stored at 120° C. for 1 hour. The reaction mixture was cooled, dissolved in DCM and washed with aqueous ammonia The organic layer was separated, dried (MgSO₄), filtered and the solvent was evaporated. The residue was purified by column chromatography over silica gel (eluent: DCM/(MeOH/NH₃) 92/8). The pure fractions were collected and the solvent was evaporated. The residue was suspended in DIPE. The precipitate was filtered off and dried (vacuum; 70° C.), yielding 3.72 g (60%) of compound 2, melting point 178.4° C.

EXAMPLE B3

Preparation of Compound 3

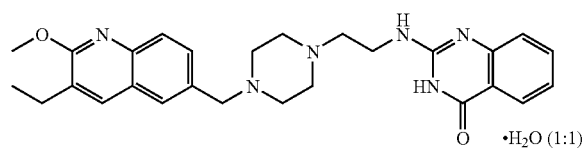 [SMILES: CCc1cc2cc(CN3CCN(CCNc4nc5ccccc5c(=O)[nH]4)CC3)ccc2nc1OC]

A mixture of intermediate 6(0.0124 mol), intermediates (0.0137 mol) and potassium carbonate (0.0373 mol) in DMF (80 ml) was stirred at 60° C. for 1 hour, poured out into ice water and stirred at room temperature for 30 min. The precipitate was filtered off, washed with water and taken up in 2-propanone. The precipitate was filtered off and dried, yielding 1.5 g (26%) of compound 3, melting point 118° C.

TABLE F-1 lists the compounds that were prepared according to one of the above Examples.

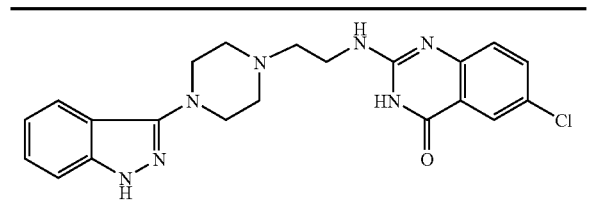

Co. No. 1; Ex. [B1]; mp. 186° C.

TABLE F-1-continued lists the compounds that were prepared according to one of the above Examples.

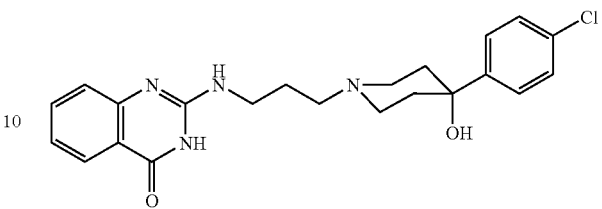

Co. No. 2; Ex. [B2]; mp. 178.4° C.

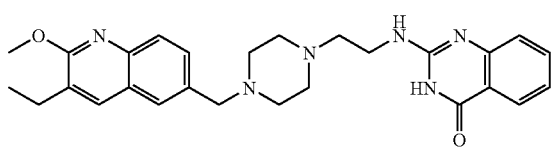 [SMILES: CCc1cc2cc(CN3CCN(CCNc4nc5ccccc5c(=O)[nH]4)CC3)ccc2nc1OC]

.H₂O (1:1); Co. No. 3; Ex. [B3]; mp. 118° C.

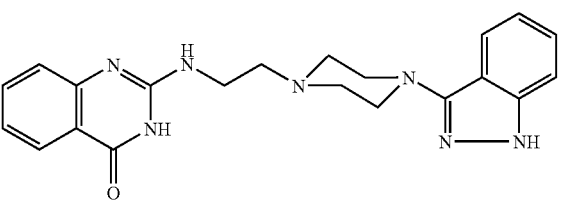 [SMILES: O=c1[nH]c(NCCN2CCN(c3n[nH]c4ccccc34)CC2)nc2ccccc12]

Co. No. 19; Ex. [B1]; mp. 206.3° C.

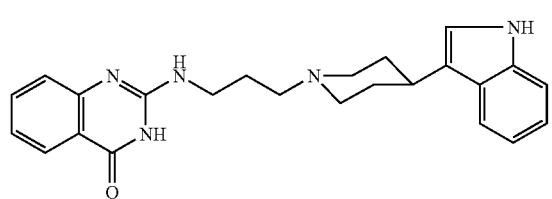 [SMILES: O=c1[nH]c(NCCCN2CCC(c3c[nH]c4ccccc34)CC2)nc2ccccc12]

Co. No. 20; Ex. [B1]; mp. 164.6° C.

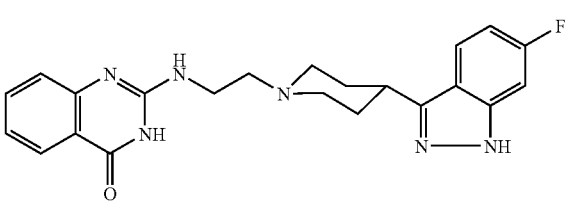 [SMILES: O=c1[nH]c(NCCN2CCC(c3n[nH]c4cc(F)ccc34)CC2)nc2ccccc12]

Co. No. 21; Ex. [B1]; mp. 193° C.

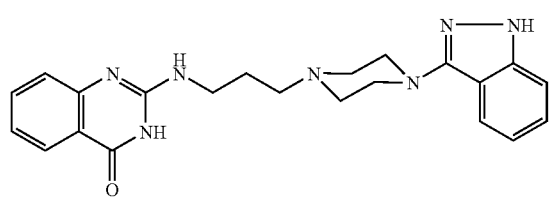 [SMILES: O=c1[nH]c(NCCCN2CCN(c3n[nH]c4ccccc34)CC2)nc2ccccc12]

Co. No. 22; Ex. [B1]; mp. 254° C.

TABLE F-1-continued lists the compounds that were prepared according to one of the above Examples.

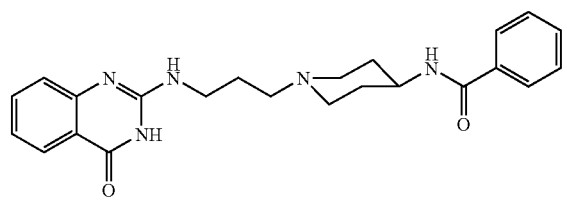 [SMILES: O=C(NC1CCN(CCCNc2nc3ccccc3c(=O)[nH]2)CC1)c1ccccc1]

Co. No. 23; Ex. [B1]; mp. 243.1° C.

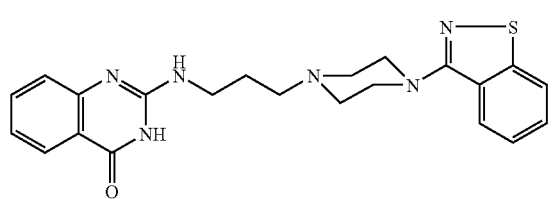

Co. No. 24; Ex. ]B1]; mp. 133.6° C.

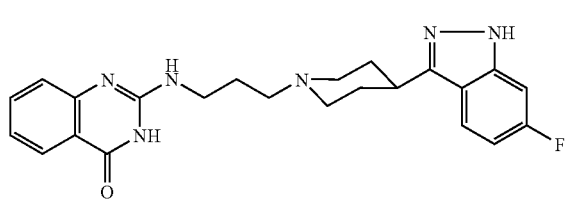

Co. No. 25; Ex. [B1]; mp. 274.4° C.

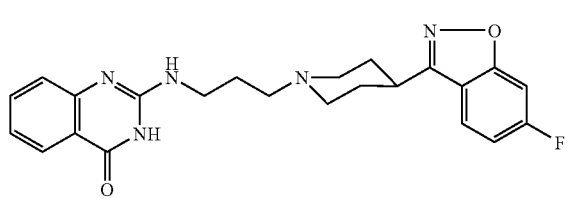 [SMILES: O=c1[nH]c(NCCCN2CCC(c3noc4cc(F)ccc34)CC2)nc2ccccc12]

.H$_2$O (2:1)•C$_4$H$_4$O$_4$ (2:1); Co. No. 26; Ex. [B1]; mp. 147.1° C.

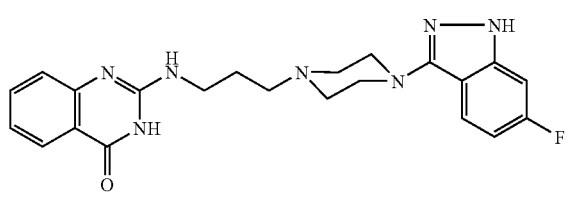 [SMILES: O=c1[nH]c(NCCCN2CCN(c3n[nH]c4cc(F)ccc34)CC2)nc2ccccc12]

Co. No. 27; Ex. [B1]; mp. 274° C.

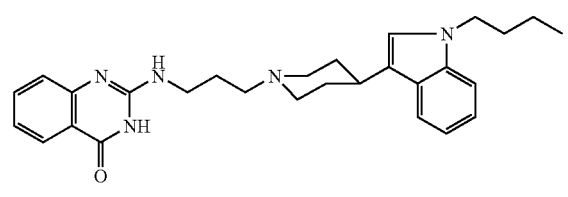 [SMILES: CCCCn1cc(C2CCN(CCCNc3nc4ccccc4c(=O)[nH]3)CC2)c2ccccc21]

Co. No. 28; Ex. [B1]; mp. 119.5° C.

TABLE F-1-continued lists the compounds that were prepared according to one of the above Examples.

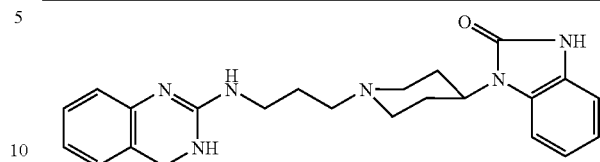

Co. No. 29; Ex. [B1]; mp. 255.5° C.

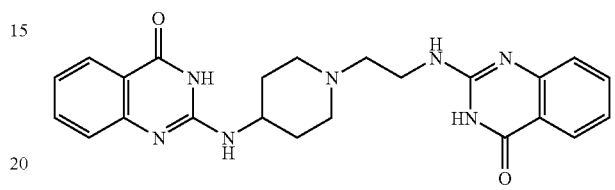

Co. No. 30; Ex. [B1]; mp. 230° C.

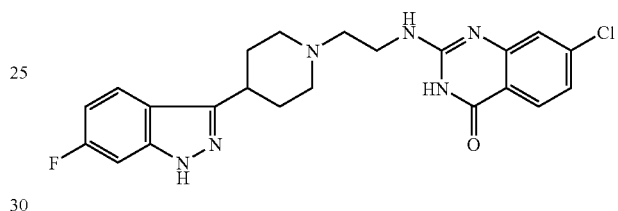

.C$_2$H$_2$O$_4$ (1:2)•H$_2$O (1:1); Co. No. 31; Ex. [B1]; mp. 142° C.

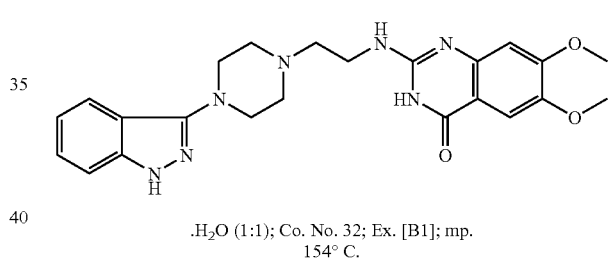

.H$_2$O (1:1); Co. No. 32; Ex. [B1]; mp. 154° C.

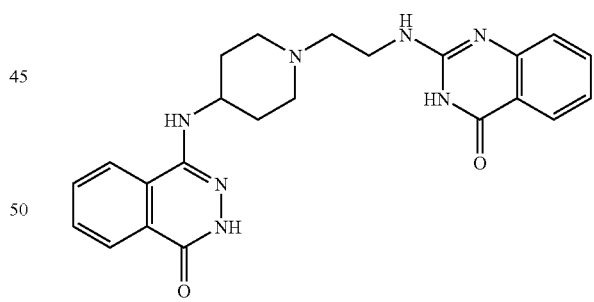

.H$_2$O (1:5); Co. No. 33; Ex. [B1]; mp. 190° C.

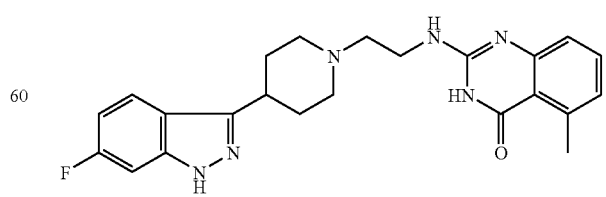

.C$_2$H$_2$O$_4$ (1:2)•H$_2$O (1:2)Co. No. 34; Ex. [B1]; mp. 156° C.

TABLE F-1-continued lists the compounds that were prepared according to one of the above Examples.

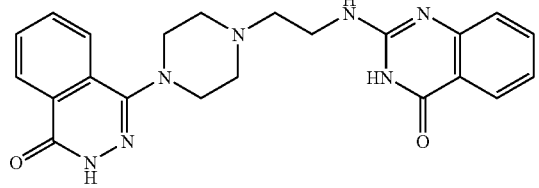

Co. No. 35; Ex. [B1]; mp. >260° C.

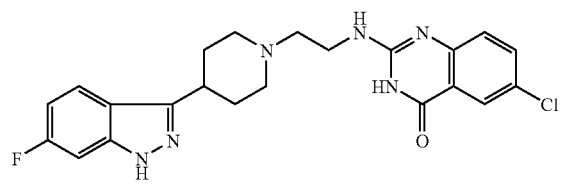 [SMILES: O=c1[nH]c(NCCN2CCC(c3n[nH]c4cc(F)ccc34)CC2)nc2ccc(Cl)cc12]

.C₂H₂O₄ (1:2)•H₂O (1:1); Co. No. 36; Ex. [B1]; mp. 134° C.

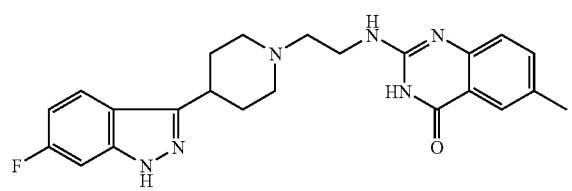 [SMILES: Cc1ccc2nc(NCCN3CCC(c4n[nH]c5cc(F)ccc45)CC3)[nH]c(=O)c2c1]

.C₂H₂O₄ (1:1); Co. No. 37; Ex. [B1]; mp. 148° C.

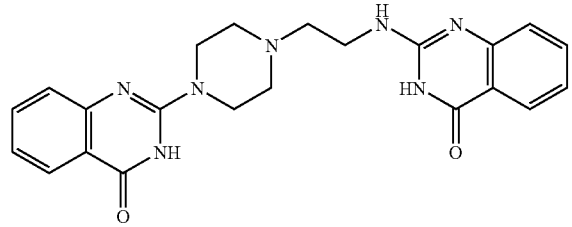 [SMILES: O=c1[nH]c(NCCN2CCN(c3nc4ccccc4c(=O)[nH]3)CC2)nc2ccccc12]

.H₂O (1:1); Co. No. 38; Ex. [B1]; mp. 205° C.

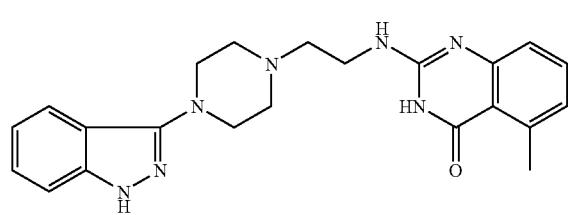 [SMILES: Cc1cccc2nc(NCCN3CCN(c4n[nH]c5ccccc45)CC3)[nH]c(=O)c12]

Co. No. 39; Ex. [B1]; mp. 172° C.

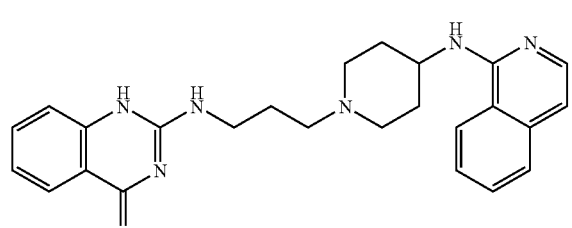

Co. No. 40; Ex. [B1]

TABLE F-1-continued lists the compounds that were prepared according to one of the above Examples.

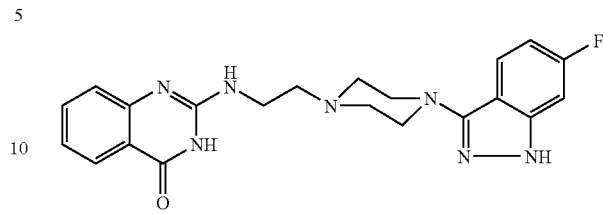

Co. No. 41; Ex. [B1]; mp. 242.2° C.

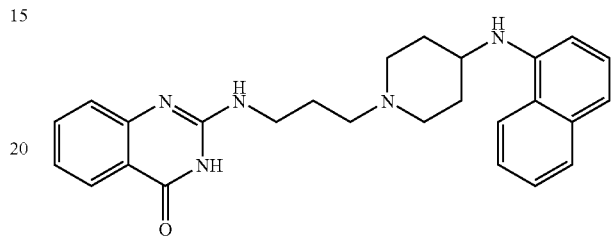

Co. No. 42; Ex. [B1]

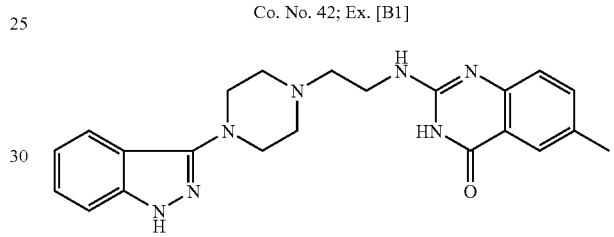

Co. No. 43; Ex. [B1]; mp. 254° C.

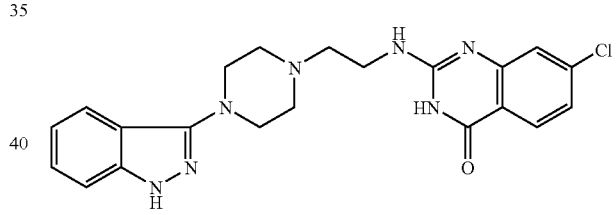

Co. No. 44; Ex. [B1]; mp. 172° C.

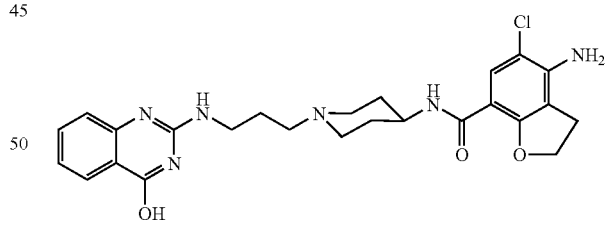

.H₂O (2:1); Co. No. 45; Ex. [B2]; mp. 192.6° C.

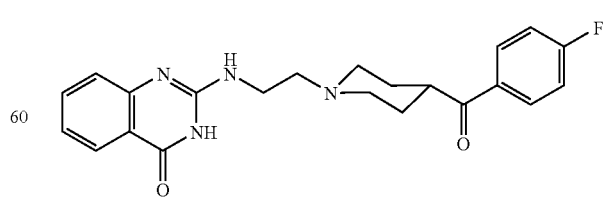

.HCl (1:2); Co. No. 46; Ex. [B1]; mp. 253.8° C.

TABLE F-1-continued
lists the compounds that were prepared according to one of the above Examples.
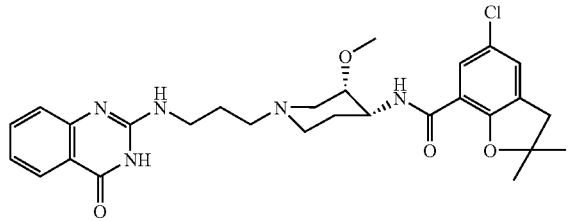
(B-CIS); Co. No. 18; Ex. [B2]; mp. 145.8° C.
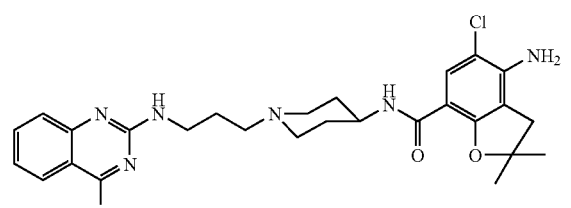
Co. No. 4; EP 669919
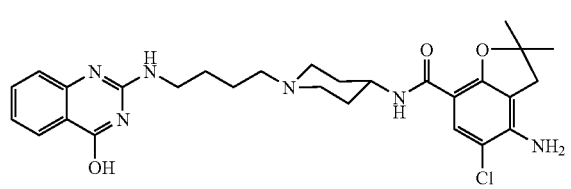 [SMILES: CC1(C)Cc2c(N)c(Cl)cc(C(=O)NC3CCN(CCCCNc4nc(O)c5ccccc5n4)CC3)c2O1]
Co. No. 5; EP669919
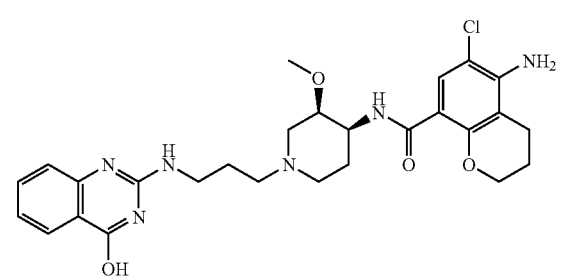 [SMILES: CO[C@@H]1CN(CCCNc2nc(O)c3ccccc3n2)CC[C@@H]1NC(=O)c1cc(Cl)c(N)c2c1OCCC2]
(CIS); Co. No. 6; US 5374637
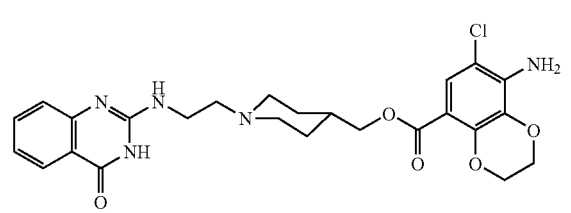 [SMILES: Nc1c(Cl)cc(C(=O)OCC2CCN(CCNc3nc4ccccc4c(=O)[nH]3)CC2)c2c1OCCO2]
Co. No. 7; EP 885190
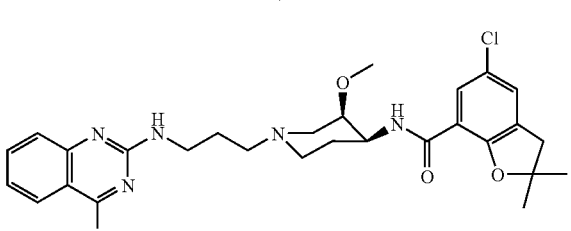
Co. No. 8; EP 669919, US 5374637
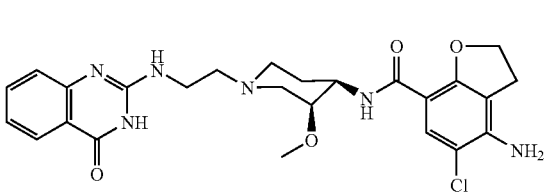
Co. No. 9, US 5374637
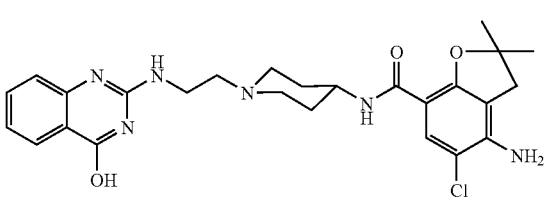 [SMILES: CC1(C)Cc2c(N)c(Cl)cc(C(=O)NC3CCN(CCNc4nc(O)c5ccccc5n4)CC3)c2O1]
Co. No. 10, EP 669919
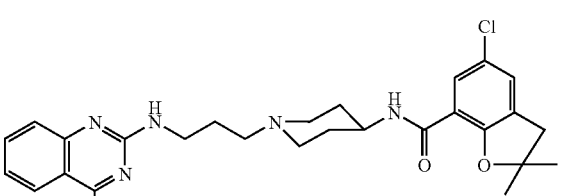
Co. No. 11, EP 669919
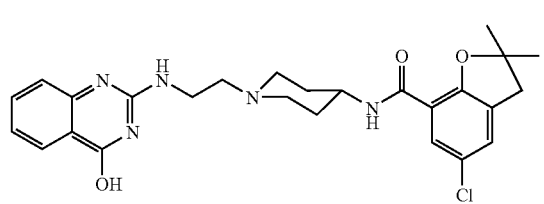 [SMILES: CC1(C)Cc2cc(Cl)cc(C(=O)NC3CCN(CCNc4nc(O)c5ccccc5n4)CC3)c2O1]
Co. No. 12, EP 669919
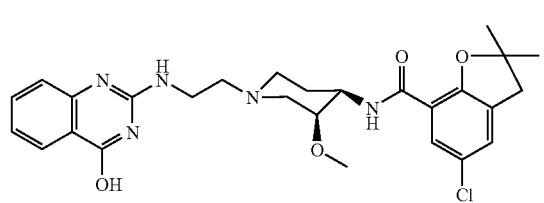
Co. No. 13, EP 669919
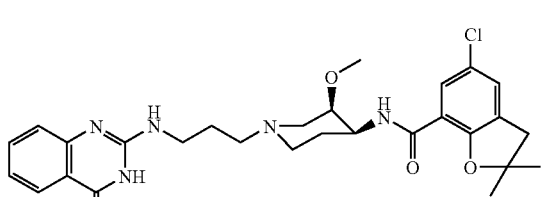
Co. No. 14, EP 669919

TABLE F-1-continued lists the compounds that were prepared according to one of the above Examples.

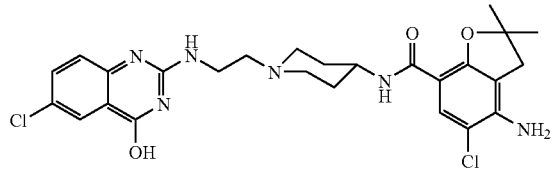 [SMILES: CC1(C)Cc2c(N)c(Cl)cc(C(=O)NC3CCN(CCNc4nc(O)c5cc(Cl)ccc5n4)CC3)c2O1]

Co. No. 15, EP 669919

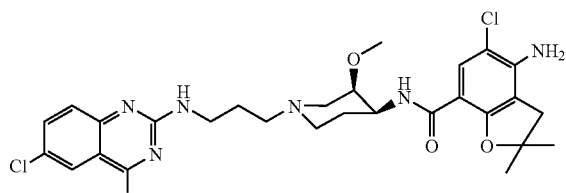

Co. No. 16, EP 669919

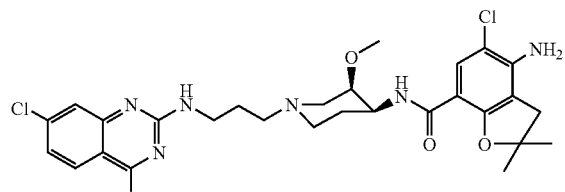

Co. No. 17, EP 669919

PHARMACOLOGICAL EXAMPLE

In vitro Scintillation Proximity Assay (SPA) for PARP-1 Inhibitory Activity

Compounds of the present invention were tested in an in vitro assay based on SPA technology (proprietary to Amersham Phannacia Biotech). In principle, the assay relies upon the well established SPA technology for the detection of poly(ADP-ribosyl)ation of biotinylated target proteins, i.e histones. This ribosylation is induced using nicked DNA activated PARP-1 enzyme and [$^3$H]-nicotinamide adenine dinucleotide ([I$^3$H]-NAD$^+$) as ADP-ribosyl donor.

As inducer of PARP-1 enzyme activity, nicked DNA was prepared. For this, 25 mg of DNA (supplier: Sigma) was dissolved in 25 ml DNAse buffer (10 MM Tris-HCl, pH 7.4; 0.5 mg/ml Bovine Serum Albumine (MSA); 5 mM MgCl$_2$.6H$_2$O and 1 mM KCl) to which 50 µl DNAse solution (1 mg/ml 0.15 M NaCl) was added. After an incubation of 90 min. at 37° C., the reaction was terminated by adding 1.45 g NaCl, followed by a further incubation at 58 ° C for 15 min. The reaction mixture was cooled on ice and dialysed at 4° C. for respectively 1.5 and 2 hours against 1.5 l of 0.2 M KCl, and twice against 1.51 of 0.01 M KCl for 1.5 and 2 h respectively. The mixture was aliquoted and stored at −20 ° C. Histones (1 mg/ml, type II-A, supplier: Sigma) were biotinylated using the biotinylation kit of Amnersham and stored aliquoted at −20 ° C. A stock solution of 100 mg/ml SPA poly(vinyl toluene) (PVT) beads (supplier: Amersham) was made in PBS. A stock solution of [$^3$H]-NAD$^+$ was made by adding 120 µl of [$^3$H]-NAD$^+$ (0.1 mCi/ml, supplier: NW to 6 ml incubation buffer (50 mM Tris/HCl, pH 8; 0.2 nM DTT; 4 mM MgCl$_2$). A solution of 4 MM NAD$^+$ (supplier: Roche) was made in incubation buffer (from a 100 mM stock solution in water stored at −20° C.) The PARP-1 enzyme was produced using aft known techniques, i.e. cloning and expression of the protein starting from human liver cDNA. Information concerning the used protein sequence of the PARP-1 enzyme including literature references can be found in the Swiss-Prot database under primary accession number P09874. Biotinylated histones and PVT-SPA beads were mixed and preincubated for 30 min. at room temperature. PARP-1 enzyme (concentration was lot dependent) was mixed with the nicked DNA and the mixture was pre-incubated for 30 min. at 4° C. Equal parts of this histones/PVT-SPA beads solution and PARP-1 enzyme/DNA solution were mixed and 75 µl of this mixture together with 1 µl of compound in DMSO and 25 µl of [$^3$H]-NAD$^+$ was added per well into a 96-well microtiterplate. The final concentrations in the incubation mixture were 2 µg/ml for the biotinylated histones, 2 mg/ml for the PVT-SPA beads, 2 µg/ml for the nicked DNA and between 5-10 µg/ml for the PARP-1 enzyme. After incubation of the mixture for 15 min. at room temperature, the reaction was terminated by adding 100 µl of 4 mM NAD$^+$ in incubation buffer (final concentration 2 mM) and plates were mixed.

The beads were allowed to sediment for at least 15 min. and plates transferred to a TopCountNXT™ (Packard) for scintillation counting, values were expressed as counts per minute (cpm). For each experiment, controls (containing PARP-1 enzyme and DMSO without compound), a blank incubation (containing DMSO but no PARP-1 enzyme or compound) and samples (containing PARP-1 enzyme and compound dissolved in DMSO) were run in parallel. All compounds tested were dissolved and eventually further diluted in DMSO. In first instance, compounds were tested at a concentration of $10^{-5}$M. When the compounds showed activity at $10^{-5}$M, a dose-response curve was made wherein the compounds were tested at concentrations between $10^{-5}$M and $10^{-8}$M. In each test, the blank value was subtracted from both the control and the sample values. The control sample represented maximal PARP-1 enzyme activity. For each sample, the amount of cpm was expressed as a percentage of the mean cpm value of the controls. When appropriate, IC$_{50}$-values (concentration of the drug, needed to reduce the PARP-1 enzyme activity to 50% of the control) were computed using linear interpolation between the experimental points just above and below the 50% level. Herein the effects of test compounds are expressed as pIC$_{50}$ (the negative log value of the IC$_{50}$-value). As a reference compound, 4-amino-1,8-naphthalimide was included to validate the SPA assay. The tested compounds showed inhibitory activity at the initial test concentration of $10^{-5}$ M (see Tabel-2).

In vitro Filtration Assay for PARP-1 Inhibitory Activity

Compounds of the present invention were tested in an in vitro filtration assay assessing PARP-1 activity (triggered in the presence of nicked DNA) by means of its histone poly (ADP-ribosyl)ation activity using [$^{32}$P]-NAD as ADP-ribosyl donor. The radioactive ribosylated histones were precipitated by trchloroacetic acid (TCA) in 96-well filterplates and the incorporated [$^{32}$P] measured using a scintillation counter A mixture of histones (stock solution: 5 mg/ml in H$_2$O), NAD$^+$ (stock solution: 100 mM in H$_2$O), and [$^{32}$P]-NAD$^+$ in incubation buffer (50 mM Tris/HCl, pH 8; 0.2 mM DTT; 4 mM MgCl$_2$) was made. A mixture of the PARP-1 enzyme (5 -10 µg/ml) and nicked DNA was also made. The nicked DNA was prepared as described in the in vitro SPA for PARP-1 inhibitory activity. Seventy-five µl of the PARP-1 enzyme/ DNA mixture together with 1 µl of compound in DMSO and 25 µl of histones-NAD$^+$/[$^{32}$P]-NAD$^+$ mixture was added per well of a 96-well filterplate (0.45 µm, supplier Millpore). The final concentrations in the incubation mixture were 2 µg/ml for the histones, 0.1 mM for the NAD⁺, 200 µM (0.5 µC) for the [$^{32}$P]-NAD⁺ and 2 µg/ml for the nicked DNA. Plates were incubated for 15 min. at room temperature and the reaction was terminated by the addition of 10 µl ice cold 100% TCA followed by the addition of 10 µl ice-cold BSA solution (1% in H$_2$O). The protein fraction was allowed to precipitate for 10 min. at 4° C. and plates were vacuum filtered. The plates were subsequently washed with, for each well, 1 ml of 10% ice cold TCA, 1 ml of 5% ice cold TCA and 1 ml of 5% TCA at room temperature. Finally 100 µl of scintillation solution (Microscint 40, Packard) was added to each well and the plates were transferred to a TopCountNXT™ (supplier: Packard) for scintillation counting and values were expressed as counts per minute (cpm). For each experiment, controls (containing PARP-1 enzyme and DMSO without compound), a blank incubation (containing DMSO but no PARP-1 enzyme or compound) and samples (containing PARP-1 enzyme and compound dissolved in DMSO) were run in parallel. All compounds tested were dissolved and eventually further diluted in DMSO. In first instance, compounds were tested at a concentration of $10^{-5}$M. When the compounds showed activity at $10^{-5}$M, a dose-response curve was made wherein the compounds were tested at concentrations between $10^{-5}$M and $10^{-8}$M. In each test, the blank value was subtracted from both the control and the sample values. The control sample represented maximal PARP-1 enzyme activity. For each sample, the amount of cpm was expressed as a percentage of the mean cpm value of the controls. When appropriate, IC$_{50}$-values (concentration of the drug, needed to reduce the PARP-1 enzyme activity to 50% of the control) were computed using linear interpolation between the experimental points just above and below the 50% level. Herein the effects of test compounds are expressed as pIC$_{50}$ (the negative log value of the IC$_{50}$-value). As a reference compound, 4-amino-1,8-naphthalimide was included to validate the filtration assay. The tested compounds showed inhibitory activity at the initial test concentration of $10^{-5}$M (see Tabel-2).

In vitro Scintillation Proximity Assay (SPA) for TANK-2 Inhibitory Activity

Compounds of the present invention were tested in an in vitro assay based on SPA technology with Ni Flash plates (96 or 384 well).

In principle, the assay relies upon SPA technology for the detection of auto-poly(ADP-ribosyl)ation of TANK-2 protein using [$^3$H]-nicotinamide adenine dinucleotide ([$^3$H]-NAD⁺) as ADP-ribosyl donor.

A stock solution of [$^3$H]-NAD⁺/NAD was made by adding 64.6 µl of [$^3$H]-NAD⁺ (0.1 mCi/ml, supplier Perkin Elmer) and 46.7 µl NAD-stock (10.7 mM, stored at −20° C., supplier Roche) to 1888.7 µl assay buffer (60 mM Tris/HCl, pH 7.4; 0.9 mM DTT; 6 mM MgCl$_2$). The TANK-2 enzyme was produced as described in EP1238063. 60 µL of assay buffer, together with 1 µl of compound in DMSO, 20 µl of [$^3$H]-NAD⁺/NAD and 20 µl of TANK-2 enzyme (final concentration 6 µg/ml) was added per well into a 96-well Ni-coated flash plate (Perlin Elmer). After incubation of the mixture for 120 min. at room temperature, the reaction was terminated by adding 60 µl of stopsolution (42.6 mg NAD in 6 ml H$_2$O). The plates were covered with a plate sealer and placed in a TopCountNXT™ (Packard) for scintillation counting. Values were expressed as counts per minute (cpm). For each experiment, controls (containing TANK-2 enzyme and DMSO without compound), a blank incubation (containing DMSO but no TANK-2 enzyme or compound) and samples (containing TANK-2 enzyme and compound dissolved in DMSO) Were run in parallel. All compounds tested were dissolved and eventually further diluted in DMSO. In first instance, compounds were tested at a concentration of $10^{-5}$M. When the compounds showed activity at $10^{-5}$M, a dose-response curve was made wherein the compounds were tested at concentrations between $10^{-5}$M and $10^{-8}$CM. In each test, the blank value was subtracted from both the control and the sample values. The control sample represented maximal TANK-2 enzyme activity For each sample, the amount of cpm was expressed as a percentage of the mean cpr value of the controls. When appropriate, IC$_{50}$-values (concentration of the drug, needed to reduce the TANK-2 enzyme activity to 50% of the control) were computed using linear interpolation between the experimental points just above and below the 50% level. Herein the effects of test compounds are expressed as pIC$_{50}$ (the negative log value of the IC$_{50}$-value). As reference compounds, 3-aminobenzamide and 4-amino-1,8-naphtalimide were included to validate the SPA assay. Herein the assay was described using 96-well plates. In the assay using 384-well plates the same final concentrations were used and volumes were adapted. If 96-well plate results were available these results were incorporated in Table-2, otherwise the results from the 384-well plate assay were shown.

TABEL 2

| Compound No | in vitro filter assay PARP-1 pIC50 | in vitro SPA assay PARP-1 pIC50 | in vitro SPA assay TANK-2 pIC50 |
|---|---|---|---|
| 1 | | 8.11 | <5 |
| 2 | 6.012 | 6.876 | <5 |
| 3 | | 6.272 | 5.753 |
| 4 | 5.438 | 6.144 | <5 |
| 5 | 5.579 | 6.195 | <5 |
| 6 | 5.563 | 6.412 | <5 |
| 7 | 5.464 | 6.228 | 6.127 |
| 8 | 5.676 | 6.272 | <5 |
| 11 | | | <5 |
| 12 | | | <5 |
| 13 | | | <5 |
| 16 | | | <5 |
| 17 | | | <5 |
| 18 | 5.345 | 6.072 | <5 |
| 19 | 6.204 | 7.498 | <5 |
| 20 | 5.276 | 6.171 | <5 |
| 21 | 6.284 | 7.593 | <5 |
| 22 | 6.331 | 7.334 | 5.073 |
| 23 | 5.595 | 6.163 | <5 |
| 24 | 5.305 | 6.105 | <5 |
| 25 | 5.635 | 6.721 | <5 |
| 26 | 5.789 | 6.372 | <5 |
| 27 | 6.373 | 7.353 | 5.099 |
| 28 | 5.55 | 5.827 | <5 |
| 29 | 5.333 | 6.105 | <5 |
| 30 | | 7.491 | 6.1 |
| 31 | | 7.405 | <5 |
| 32 | | 7.345 | |
| 33 | | 7.458 | 6.028 |
| 34 | | 7.664 | |
| 35 | | 7.971 | |
| 36 | | 7.965 | <5 |
| 37 | | 7.816 | <5 |
| 38 | | 6.373 | 6.27 |
| 39 | | 8.003 | <5 |
| 40 | 5.649 | 6.492 | <5 |
| 41 | 6.263 | 7.352 | <5 |
| 42 | 5.048 | 6.075 | <5 |
| 43 | | 7.908 | <5 |
| 44 | | 7.533 | <5 |
| 45 | 5.516 | 6.647 | <5 |
| 46 | 5.729 | 6.637 | <5 |

The compounds can be further evaluated in a cellular chemo- and/or radiosensitization assay, an assay measuring inhibition of endogenous PARP-1 activity in cancer cell lines and eventually in an in vivo radiosensitization test.

The invention claimed is:

1. A compound of formula (I),

Z—L—X    N—C$_{1-6}$alkanediyl-NH    (I)

(with R$^2$ on X, and the right-hand ring bearing R$^1$, R$^3$, and Y)

the N-oxide forms, the pharmaceutically acceptable addition salts and the stereo-chemically isomeric forms thereof, wherein
the dotted lines represent optional bonds:
X is >N—
—N═══Y— is —N—C(O)— or —N═CR$^4$—, wherein R$^4$ is hydroxy;
L is a direct bond or a bivalent radical selected from —C(O)—, —C(O)—NH—, —NH—, —C(O)—C$_{1-6}$alkanediyl-, —C(O)—O—C$_{1-6}$alkanediyl- or —C$_{1-6}$alkanediyl-;
R$^1$ is hydrogen, halo, C$_{1-6}$alkyloxy or C$_{1-6}$alkyl;
R$^2$ is hydrogen, hydroxy, C$_{1-6}$alkyloxy or aminocarbonyl;
when X is substituted with R$^2$ than R$^2$ taken together with -L-Z can form a bivalent radical of formula —C(O)—NH—CH$_2$—NR$^{10}$—    (a-1)

wherein R$^{10}$ is phenyl;
R$^3$ is hydrogen, or C$_{1-6}$alkyloxy;
Z is (b-7)

(indazole structure with R$^5$)

wherein each R$^5$, R$^6$, R$^7$ and R$^8$ is independently selected from hydrogen, halo, amino, C$_{1-6}$alkyl or C$_{1-6}$alkyloxy; or
R$^7$ and R$^8$ taken together may form a bivalent radical of formula —CH$_2$—CR$^9$$_2$—O—    (c-1), —(CH$_2$)$_3$—O—    (c-2), —O—(CH$_2$)$_2$—O—    (c-3) or —CH═CH—CH═CH—    (c-4)

wherein each R$^9$ is independently selected from hydrogen or C$_{1-6}$alkyl.

2. A compound as claimed in claim 1 wherein
L is a direct bond or a bivalent radical selected from —C(O)—, —C(O)—NH—, or —C(O)—O—C$_{1-6}$alkanediyl-; R$^2$ is hydrogen, hydroxy, or C$_{1-6}$alkyloxy; each R$^5$, R$^6$, R$^7$ and R$^8$ is independently selected from hydrogen, halo, amino, C$_{1-6}$alkyl or C$_{1-6}$alkyloxy; or R$^7$ and R$^8$ taken together may form a bivalent radical of formula (c-1), (c-2), (c-3) or (c-4).

3. A compound according to claim 1 wherein
L is a direct bond; R$^1$ is hydrogen, halo or C$_{1-6}$alkyl;
R$^2$ is hydrogen; and each R$^5$ is independently selected from hydrogen or halo.

4. A compound according to claim 1, 2, or 3 wherein the compound is selected from Compound 39

Compound 1 and

Compound 43

5. A pharmaceutical composition comprising pharmaceutically acceptable carriers and as an active ingredient a therapeutically effective amount of a compound as claimed in claim 1.

6. A process of preparing a pharmaceutical composition as claimed in claim 5 wherein the pharmaceutically acceptable carriers and the compound as claimed in claim 1 are intimately mixed.

7. A method of alleviating colon cancer, breast cancer, melanoma, glioblastoma, or lymphoma; protecting against cardiac dysfunction associated with doxorubicin; exhibiting a nephroprotective effect against ischemia-reperfusion injury; or protecting against peripheral neuropathy associated with cisplatin or taxol in a subject, said method comprising administering to the subject a therapeutically effective amount of a pharmaceutical composition comprising a pharmaceutically acceptable carrier and a compound claim 1.

8. The method of claim 7, wherein the alleviation involves chemosensitization.

9. The method of claim 7, wherein the alleviation involves radiosensitization.

10. A combination of a compound with a chemotherapeutic agent wherein said compound is a compound of claim 1.

11. A process for preparing a compound as claimed in claim 1, said process comprising:
reacting an intermediate of formula (II) with an intermediate of formula (III), wherein W is an appropriate leaving group, with the formation of a compound of formula (I) and both dotted lines can be a bond, in a reaction-inert solvent and with the addition of an appropriate base,

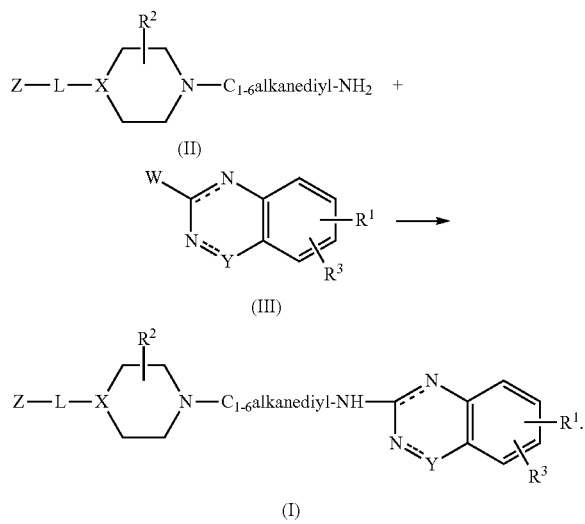

12. A pharmaceutical composition comprising pharmaceutically acceptable carriers and as an active ingredient a therapeutically effective amount of a compound as claimed in claim 2.

13. A pharmaceutical composition comprising pharmaceutically acceptable carriers and as an active ingredient a therapeutically effective amount of a compound as claimed in claim 3.

14. A pharmaceutical composition comprising pharmaceutically acceptable carriers and as an active ingredient a therapeutically effective amount of a compound as claimed in claim 4.

15. A method of alleviating colon cancer, breast cancer, melanoma, glioblastoma, or lymphoma; protecting against cardiac dysfunction associated with doxorubicin; exhibiting a nephroprotective effect against ischemia-reperfusion injury; or protecting against peripheral neuropathy associated with cisplatin or taxol in a subject, said method comprising administering to the subject a therapeutically effective amount of a pharmaceutical composition comprising a pharmaceutically acceptable carrier and a compound of claim 2.

16. A method of alleviating colon cancer, breast cancer, melanoma, glioblastoma, or lymphoma; protecting against cardiac dysfunction associated with doxorubicin; exhibiting a nephroprotective effect against ischemia-reperfusion injury; or protecting against peripheral neuropathy associated with cisplatin or taxol in a subject, said method comprising administering to the subject a therapeutically effective amount of a pharmaceutical composition comprising a pharmaceutically acceptable carrier and a compound of claim 3.

17. A method of alleviating colon cancer, breast cancer, melanoma, glioblastoma, or lymphoma; protecting against cardiac dysfunction associated with doxorubicin; exhibiting a nephroprotective effect against ischemia-reperfusion injury; or protecting against peripheral neuropathy associated with cisplatin or taxol in a subject, said method comprising administering to the subject a therapeutically effective amount of a pharmaceutical composition comprising a pharmaceutically acceptable carrier and a compound of claim 4.

* * * * *

UNITED STATES PATENT AND TRADEMARK OFFICE
CERTIFICATE OF CORRECTION

PATENT NO. : 8,623,872 B2  Page 1 of 1
APPLICATION NO. : 11/569892
DATED : January 7, 2014
INVENTOR(S) : Guillemont et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1556 days.

Signed and Sealed this
Twenty-second Day of September, 2015

Michelle K. Lee
*Director of the United States Patent and Trademark Office*